(12) United States Patent
Filvaroff et al.

(10) Patent No.: US 8,790,646 B2
(45) Date of Patent: Jul. 29, 2014

(54) COMPOSITIONS AND METHODS FOR MODULATING VASCULAR DEVELOPMENT

(75) Inventors: Ellen Filvaroff, San Francisco, CA (US); Weilan Ye, Foster City, CA (US); Leon H. Parker, IV, San Francisco, CA (US); Jo-Anne S. Hongo, Redwood City, CA (US); Maike Schmidt, San Francisco, CA (US)

(73) Assignee: Genentech Inc., South San Francisco, CA (US)

( * ) Notice: Subject to any disclaimer, the term of this patent is extended or adjusted under 35 U.S.C. 154(b) by 0 days.

(21) Appl. No.: 12/904,813

(22) Filed: Oct. 14, 2010

(65) Prior Publication Data
US 2012/0003208 A1 Jan. 5, 2012

Related U.S. Application Data

(63) Continuation of application No. 12/357,819, filed on Jan. 22, 2009, now abandoned, which is a continuation of application No. 11/546,760, filed on Oct. 12, 2006, now abandoned, which is a continuation of application No. PCT/US2005/013658, filed on Apr. 14, 2005.

(60) Provisional application No. 60/562,054, filed on Apr. 14, 2004.

(51) Int. Cl.
*A61K 39/395* (2006.01)

(52) U.S. Cl.
USPC ...................................... 424/138.1

(58) Field of Classification Search
None
See application file for complete search history.

(56) References Cited

U.S. PATENT DOCUMENTS

| | | |
|---|---|---|
| 6,820,632 B2 | 11/2004 | Ohmi et al. |
| 6,916,648 B2 | 7/2005 | Goddard et al. |
| 6,962,797 B2 | 11/2005 | Goddard et al. |
| 6,972,325 B2 | 12/2005 | Fong et al. |
| 6,974,696 B2 | 12/2005 | Botstein et al. |
| 7,019,115 B2 | 3/2006 | Desnoyers et al. |
| 7,019,124 B2 | 3/2006 | Desnoyers et al. |
| 7,029,874 B2 | 4/2006 | Desnoyers et al. |
| 7,037,710 B2 | 5/2006 | Goddard et al. |
| 7,067,636 B2 | 6/2006 | Desnoyers et al. |
| 7,074,593 B2 | 7/2006 | Goddard et al. |
| 7,084,258 B2 | 8/2006 | Desnoyers et al. |
| 7,087,428 B2 | 8/2006 | Goddard et al. |
| 7,105,335 B2 | 9/2006 | Goddard et al. |
| 7,105,640 B2 | 9/2006 | Desnoyers et al. |
| 7,109,305 B2 | 9/2006 | Baker et al. |
| 7,112,657 B2 | 9/2006 | Goddard et al. |
| 7,115,415 B2 | 10/2006 | Goddard et al. |
| 7,132,283 B2 | 11/2006 | Fong et al. |
| 7,135,334 B2 | 11/2006 | Goddard et al. |
| 7,164,007 B2 | 1/2007 | Goddard et al. |
| 7,164,009 B2 | 1/2007 | Goddard et al. |
| 7,166,700 B2 | 1/2007 | Goddard et al. |
| 7,169,912 B2 | 1/2007 | Desnoyers et al. |
| 7,189,529 B2 | 3/2007 | Desnoyers et al. |
| 7,192,589 B2 | 3/2007 | Ashkenazi et al. |
| 7,193,049 B2 | 3/2007 | Desnoyers et al. |
| 7,193,050 B2 | 3/2007 | Baker et al. |
| 7,195,760 B2 | 3/2007 | Desnoyers et al. |
| 7,196,165 B2 | 3/2007 | Ashkenazi et al. |
| 7,196,176 B2 | 3/2007 | Goddard et al. |
| 7,202,335 B2 | 4/2007 | Goddard et al. |
| 7,202,338 B2 | 4/2007 | Goddard et al. |
| 7,208,575 B2 | 4/2007 | Desnoyers et al. |
| 7,214,656 B2 | 5/2007 | Desnoyers et al. |
| 7,220,835 B2 | 5/2007 | Baker et al. |
| 7,232,889 B2 | 6/2007 | Goddard et al. |
| 7,250,495 B2 | 7/2007 | Goddard et al. |
| 7,265,210 B2 | 9/2007 | Goddard et al. |
| 7,279,553 B2 | 10/2007 | Goddard et al. |
| 7,285,623 B2 | 10/2007 | Gao et al. |
| 7,294,700 B2 | 11/2007 | Goddard et al. |
| 7,368,250 B2 | 5/2008 | Goddard et al. |
| 7,371,836 B2 | 5/2008 | Desnoyers et al. |
| 7,419,663 B2 | 9/2008 | Ashkenazi et al. |
| 7,495,083 B2 | 2/2009 | Goddard et al. |
| 7,514,538 B2 | 4/2009 | Goddard et al. |
| 7,589,172 B2 | 9/2009 | Goddard et al. |
| 7,741,056 B2 | 6/2010 | Ashkenazi et al. |
| 7,771,719 B1 | 8/2010 | Filvaroff et al. |
| 8,007,798 B2 | 8/2011 | Ashkenazi et al. |
| 8,034,342 B2 | 10/2011 | Chen et al. |
| 8,088,386 B2 | 1/2012 | Ashkenazi et al. |
| 2003/0166907 A1* | 9/2003 | Sheppard et al. ............ 536/23.5 |

(Continued)

FOREIGN PATENT DOCUMENTS

DE 19817946 10/1999
WO WO-8703284 A1 6/1987

(Continued)

OTHER PUBLICATIONS

Caetano et al, Protein Expression and Purification, 2006, 46:136-142, IDS.*
Schmidt et al, Development, 2007, 134:2913-2923, IDS.*
Parker et al (Nature, 2004, 428:754-758, IDS).*
Auerbach et al (Clinical Chemistry, 2003, 49:32-40).*
iHOP (information hyperlinked over proteins), "EGFL7" printed Mar. 6, 2012.*
Kuhnert et al (Development 2008, 135:3989-3993).*
Rak et al.,"Consequences of angiogenesis for tumor progression, metastasis and cancer therapy," *Anti-cancer Drugs*, 6:3-18 (1995).
Office Action for Canadian Application No. 2,563,445, dated Apr. 12, 2012.

(Continued)

*Primary Examiner* — Laura B Goddard
(74) *Attorney, Agent, or Firm* — Clark & Elbing LLP; Karen L. Elbing

(57) ABSTRACT

The present invention provides methods of using EGFL7 antagonist to modulate vascular development. Also provided herein are methods of screening for modulators of EGFL7 activity. Furthermore, methods of treatment using EGFL7 antagonists are provided.

18 Claims, 11 Drawing Sheets

(56) References Cited

U.S. PATENT DOCUMENTS

| | | |
|---|---|---|
| 2003/0224984 A1 | 12/2003 | Baker et al. |
| 2004/0043927 A1 | 3/2004 | Baker et al. |
| 2004/0043972 A1 | 3/2004 | Ralf et al. |
| 2007/0020735 A1 | 1/2007 | Chen et al. |
| 2007/0031437 A1 | 2/2007 | Filvaroff et al. |
| 2008/0160021 A1 | 7/2008 | Chen et al. |
| 2009/0297512 A1 | 12/2009 | Filvaroff et al. |
| 2012/0058909 A1 | 3/2012 | Chen et al. |
| 2012/0064073 A1 | 3/2012 | Chen et al. |
| 2012/0189626 A1 | 7/2012 | Ashkenazi et al. |

FOREIGN PATENT DOCUMENTS

| | | |
|---|---|---|
| WO | WO-8801166 A1 | 2/1988 |
| WO | 98/57983 A2 | 12/1998 |
| WO | 99/46281 | 9/1999 |
| WO | 99/54437 | 10/1999 |
| WO | 00/34477 | 6/2000 |
| WO | 00/53752 | 9/2000 |
| WO | 00/58473 | 10/2000 |
| WO | 01/02563 | 1/2001 |
| WO | 01/54477 | 8/2001 |
| WO | 02/00690 | 1/2002 |
| WO | 02/08284 | 1/2002 |
| WO | WO-02076486 A2 | 10/2002 |
| WO | 2004/076482 | 9/2004 |
| WO | 2004/076482 A1 | 9/2004 |

OTHER PUBLICATIONS

Office Action for Canadian Application No. 2,563,445, dated Apr. 11, 2013.

Office Action for Japanese Application No. 2007-508646, dated Feb. 9, 2012.

Caetano, et al., "Expression and purification of recombinant vascular endothelial-statin" *Protein Expression & Purification* 46:136-142 (202), 2006.

Fitch et al., "Egfl7, a novel epidermal growth factor-domain gene expressed in endothelial cells" *Dev Dyn.* 230(2):316-324 (Jun. 2004).

Parker et al., "The endothelial-cell-derived secreted factor Egfl7 regulates vascular tube formation" *Nature* 428(6984):754-758 (Apr. 15, 2004).

Schmidt, et al., "EGFL7 regulates the collective migration of endothelial cells by restricting their spatial distribution" *Development* 134:2913-2923 (2007).

Soncin et al., "VE-statin, an endothelial repressor of smooth muscle cell migration" *EMBO Journal* 22(21):5700-5711 (Nov. 3, 2003).

Stinchcombe, et al., "Bevacizumab in the treatment of non-small cell lung cancer" (2007) *Oncogene* 26:3691-3698 (2007).

Zips et al., "New anticancer agents: in vitro and in vivo" *In Vivo* 19:1-7 (2005).

Office Action for Canadian Application No. 2563445, dated Mar. 19, 2014.

* cited by examiner

FIG. 1A

```
TGAACAGTCT TGTGCAAACG GAGGCTCGTG CCTGTCTGAG AATCACTGTG AGGATGGACA GGACGATTCT    481
 E  Q  S    C  A  N  G   E  A  R   P  V  *  E    I  T  V   R  W  T   G  R  F  C

GCCAAATAGA TGTGGACGAG TGTAAGGAGG CTCAGCACTG CTCTCAGAAG TGTGTGAATA CGCTGGGCAG TTTTCAATGT    561
 A  K  *    C  G  R    V  R  R    L  S  T   A  L  R  S   V  C  E    R  W  A    F  Q  C

GTGTGTGAGG AGGGATTCAG TTTGGACGAA GATAAAGTCA CATGTTCAAA AAATCCTGCT TCCTCACGGA ACACTGGTGG    641
 V  C  E  E   G  F  S    L  D  E   D  K  V  T   H  V  Q   K  S  C    F  L  T  E   H  W  W

AGGTTTGGGG TTGGTGGAGA ACGTTACTGA AGAGGTTCAG ATCCTAAAAA ACCGAGTGGA GCTCCTGGAG CAGAAACTGG    721
 G  L  G    L  V  E  N   V  T  E   E  V  Q    I  L  K  N   R  V  E    L  L  E   Q  K  L  E

AGATGGTTCT AGCACCCTTC ACCACCCTCC TACCTCTGGA TGGAGCAGGG GACACCAACA GCTTCCTGTC TGAGCGAACC    801
 M  V  L    A  P  F    T  T  L  L   P  L  D   G  A  G    D  T  N  S   F  L  S   E  R  T

AACTTCCTGT CCCACTCTCT GCAGCAGCTG GACCGCATCG AGTCGCTCAG CGAACAGGTC GGCTTCCTGG AGGAGAGAAT    881
 N  F  L  S    H  S  L   Q  Q  L    D  R  I   E  S  L  S    E  Q  V   G  F  L  E    E  R  I

CGGAGCCTGT GGCTGTGCAG GATCAACGCC ATCACTGATC ACAGGCTGAC CCATCAAACA TGTTCTCAAG    961
 R  S  L    G  L  C  R   D  Q  R    H  H  *  S   Q  A  D   T  S  K  H   V  L  K

AACACGAGGG AAATCATGTT GAAACTCTTT ATTTGGCACA CGAGCCGGTG ATTGATATTG TTCATGTCGT GTCATTTAAC   1041
TGTTGTGTAA GTTTGAGTCA GGAGAAATGT AAATTTATGT ATTTATAATT CCATGTTCTC GTCATGAGTT ATGCTTTTTG   1121
GATAAGTTGC ATTCCTTTTT TACGTCTCAT TTTGTGTAAT AAATCTTAAA AAAAAAAAAA AAAAAAAAAA   1201
AAAA (SEQ ID NO:5)
```

FIG. 1B-2

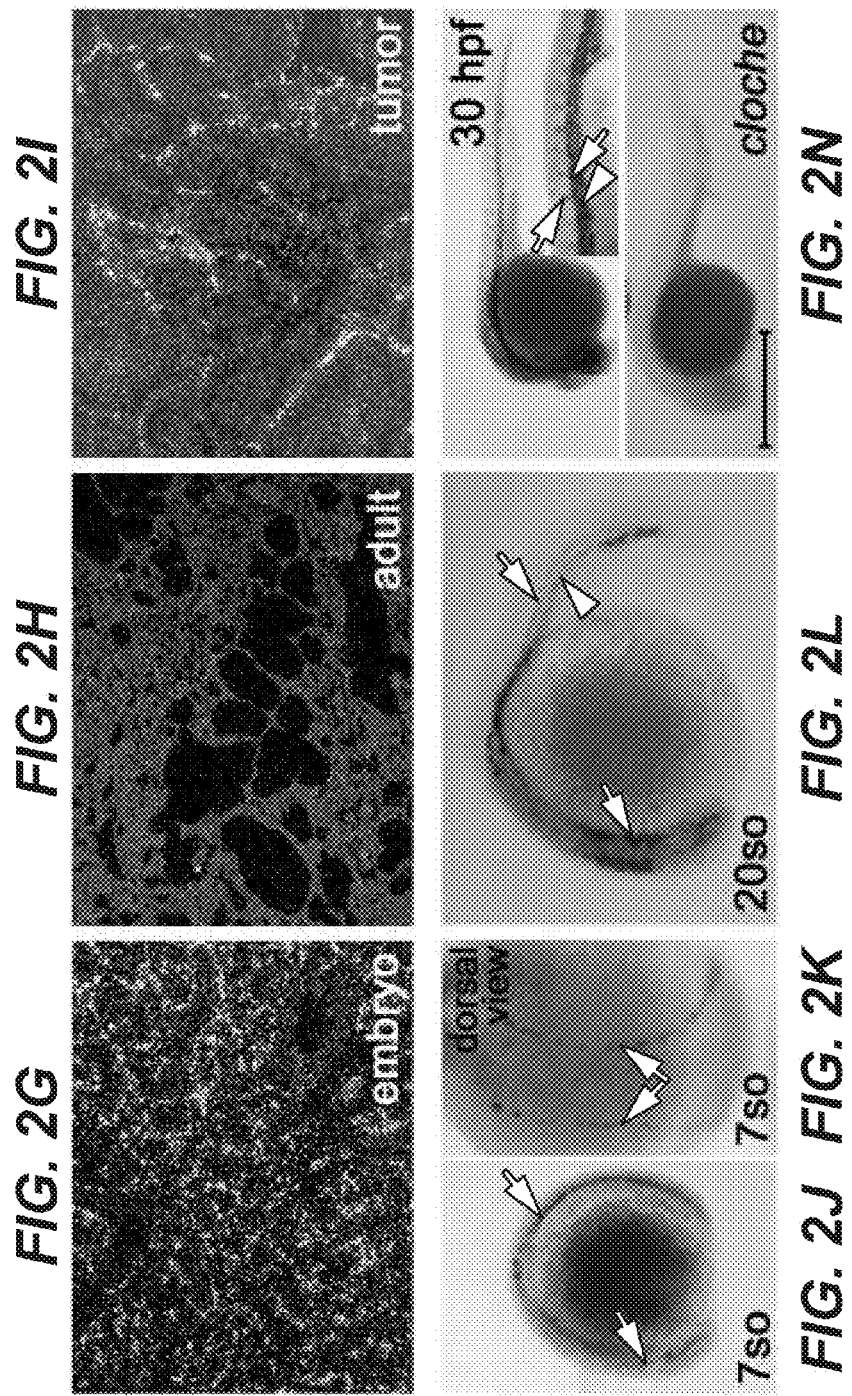

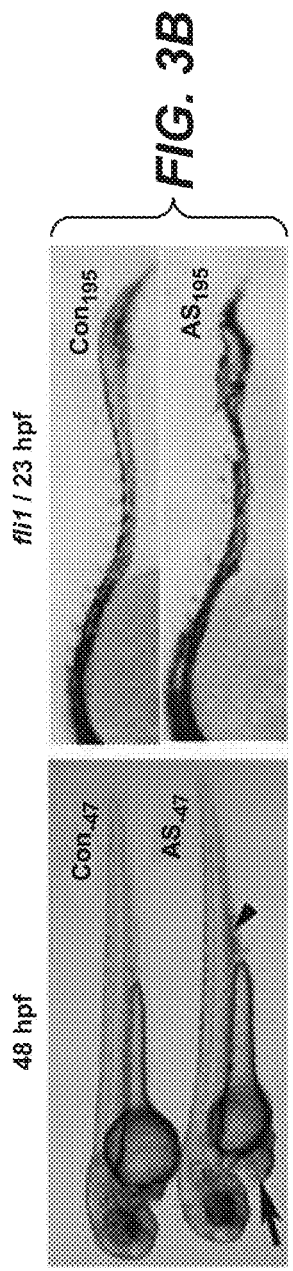
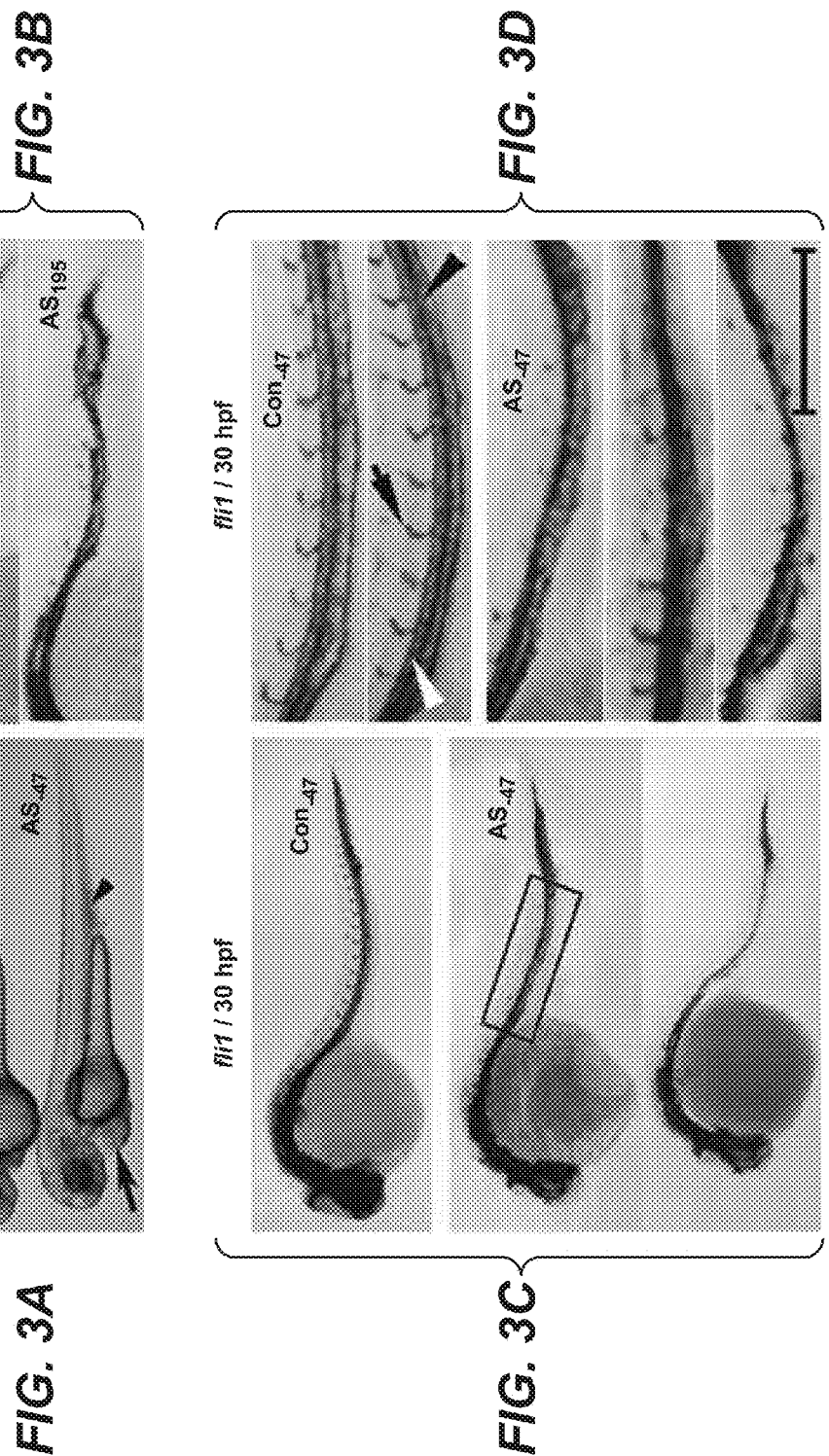

FIG. 4A
Con$_{-47}$ / 22 somites
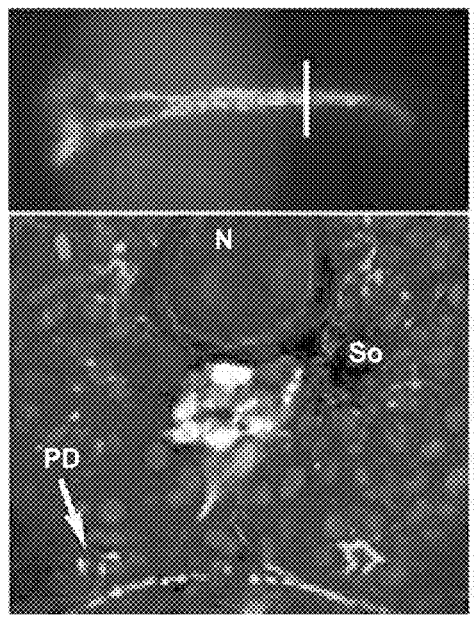
Con$_{-47}$ / 22 somites
FIG. 4C
FIG. 4B
AS$_{-47}$ / 22 somites
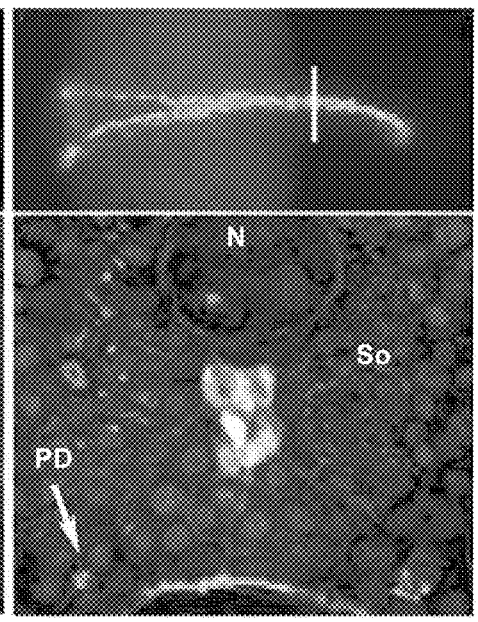
AS$_{-47}$ / 22 somites
FIG. 4D
FIG. 4E
Con$_{-47}$ / 30 hpf
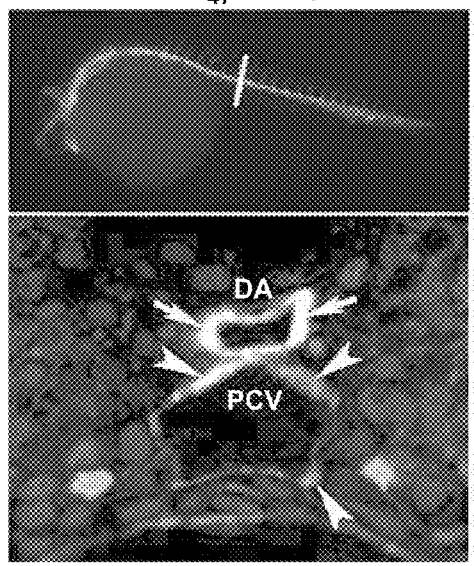
Con$_{-47}$ / 30 hpf
FIG. 4G
FIG. 4F
AS$_{-47}$ / 30 hpf
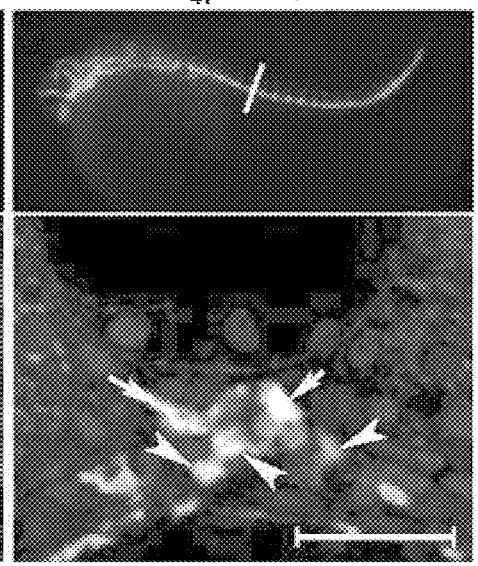
AS$_{-47}$ / 30 hpf
FIG. 4H

FIG. 5A    FIG. 5B
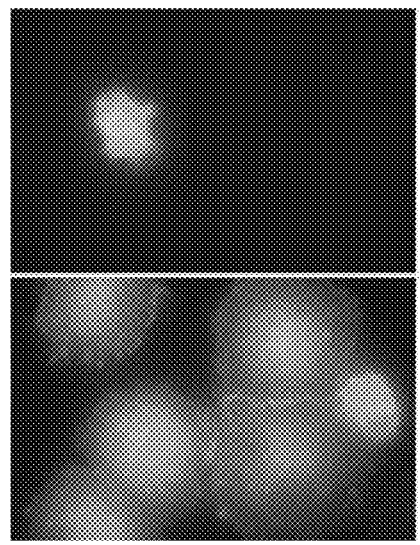 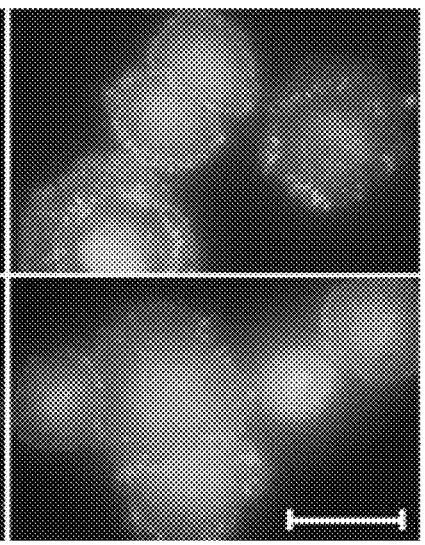
FIG. 5C    FIG. 5D
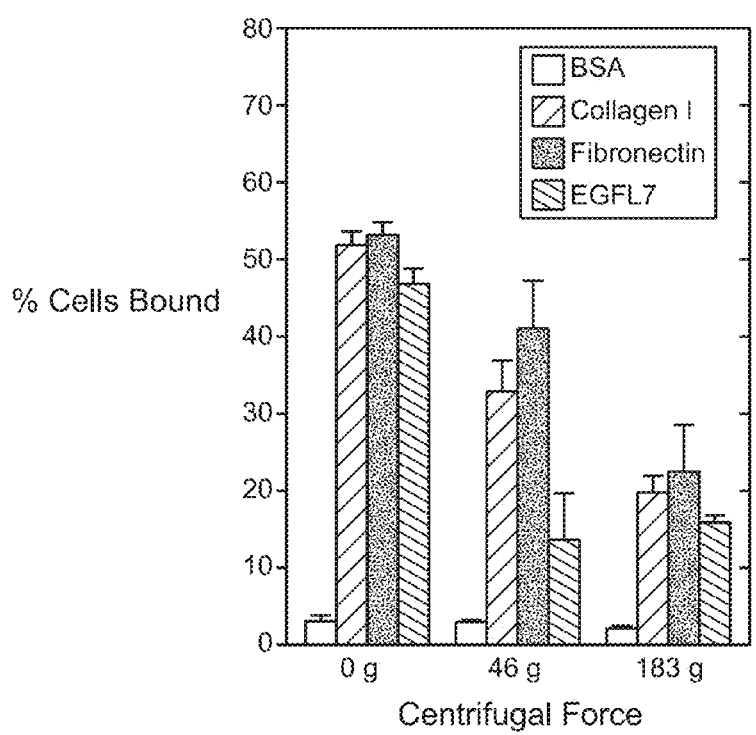
FIG. 5E

COMPOSITIONS AND METHODS FOR MODULATING VASCULAR DEVELOPMENT

RELATED APPLICATIONS

This is a Continuation of U.S. patent application Ser. No. 12/357,819 filed on Jan. 22, 2009, now abandoned, which is a continuation of Ser. No. 11/546,760, filed Oct. 12, 2006, now abandoned, which is a Continuation of Application No. PCT/US2005/013658, filed Apr. 14, 2005 under 37 CFR §1.53(b), and claims the benefit under 35 USC §119(e) of U.S. Provisional Application No. 60/562,054, filed Apr. 14, 2004.

FIELD OF THE INVENTION

The present invention relates generally to compositions and methods that are useful for modulating vascular development. Specifically, the present invention relates to EGF-like domain 7 (EGFL7), a novel endothelial cell-derived secreted factor. The present invention further relates to the diagnosis and treatment of conditions and diseases associated with angiogenesis.

BACKGROUND OF THE INVENTION

Development of a vascular supply is a fundamental requirement for many physiological and pathological processes. Actively growing tissues such as embryos and tumors require adequate blood supply. They satisfy this need by producing pro-angiogenic factors, which promote new blood vessel formation via a process called angiogenesis. Vascular tube formation is a complex but orderly biological event involving all or many of the following steps: a) Endothelial cells (ECs) proliferate from existing ECs or differentiate from progenitor cells; b) ECs migrate and coalesce to form cord-like structures; c) vascular cords then undergo tubulogenesis to form vessels with a central lumen d) existing cords or vessels send out sprouts to form secondary vessels; e) primitive vascular plexus undergo further remodeling and reshaping; and f) peri-endothelial cells are recruited to encase the endothelial tubes, providing maintenance and modulatory functions to the vessels; such cells including pericytes for small capillaries, smooth muscle cells for larger vessels, and myocardial cells in the heart. Hanahan, D. *Science* 277:48-50 (1997); Hogan, B. L. & Kolodziej, P. A. *Nature Reviews Genetics.* 3:513-23 (2002); Lubarsky, B. & Krasnow, M. A. *Cell.* 112:19-28 (2003).

It is now well established that angiogenesis is implicated in the pathogenesis of a variety of disorders. These include solid tumors and metastasis, atherosclerosis, retrolental fibroplasia, hemangiomas, chronic inflammation, intraocular neovascular diseases such as proliferative retinopathies, e.g., diabetic retinopathy, age-related macular degeneration (AMD), neovascular glaucoma, immune rejection of transplanted corneal tissue and other tissues, rheumatoid arthritis, and psoriasis. Folkman et al., *J. Biol. Chem.*, 267:10931-10934 (1992); Klagsbrun et al., *Annu. Rev. Physiol.* 53:217-239 (1991); and Garner A., "Vascular diseases", In: *Pathobiology of Ocular Disease. A Dynamic Approach*, Garner A., Klintworth GK, eds., 2nd Edition (Marcel Dekker, NY, 1994), pp 1625-1710.

In the case of tumor growth, angiogenesis appears to be crucial for the transition from hyperplasia to neoplasia, and for providing nourishment for the growth and metastasis of the tumor. Folkman et al., *Nature* 339:58 (1989). The neovascularization allows the tumor cells to acquire a growth advantage and proliferative autonomy compared to the normal cells. A tumor usually begins as a single aberrant cell which can proliferate only to a size of a few cubic millimeters due to the distance from available capillary beds, and it can stay 'dormant' without further growth and dissemination for a long period of time. Some tumor cells then switch to the angiogenic phenotype to activate endothelial cells, which proliferate and mature into new capillary blood vessels. These newly formed blood vessels not only allow for continued growth of the primary tumor, but also for the dissemination and recolonization of metastatic tumor cells. Accordingly, a correlation has been observed between density of microvessels in tumor sections and patient survival in breast cancer as well as in several other tumors. Weidner et al., *N. Engl. J. Med* 324:1-6 (1991); Horak et al., *Lancet* 340:1120-1124 (1992); Macchiarini et al., *Lancet* 340:145-146 (1992). The precise mechanisms that control the angiogenic switch is not well understood, but it is believed that neovascularization of tumor mass results from the net balance of a multitude of angiogenesis stimulators and inhibitors (Folkman, 1995, *Nat Med* 1(1): 27-31).

The process of vascular development is tightly regulated. To date, a significant number of molecules, mostly secreted factors produced by surrounding cells, have been shown to regulate EC differentiation, proliferation, migration and coalescence into cord-like structures. For example, vascular endothelial growth factor (VEGF) has been identified as the key factor involved in stimulating angiogenesis and in inducing vascular permeability. Ferrara et al., *Endocr. Rev.* 18:4-25 (1997). The finding that the loss of even a single VEGF allele results in embryonic lethality points to an irreplaceable role played by this factor in the development and differentiation of the vascular system. Furthermore, VEGF has been shown to be a key mediator of neovascularization associated with tumors and intraocular disorders. Ferrara et al., *Endocr. Rev.* supra. The VEGF mRNA is overexpressed by the majority of human tumors examined. Berkman et al., *J. Clin. Invest.* 91:153-159 (1993); Brown et al., *Human Pathol.* 26:86-91 (1995); Brown et al., *Cancer Res.* 53:4727-4735 (1993); Mattern et al., *Brit. J. Cancer* 73:931-934 (1996); Dvorak et al., *Am. J. Pathol.* 146:1029-1039 (1995).

Also, the concentration levels of VEGF in eye fluids are highly correlated to the presence of active proliferation of blood vessels in patients with diabetic and other ischemia-related retinopathies. Aiello et al., *N. Engl. J. Med.* 331:1480-1487 (1994). Furthermore, studies have demonstrated the localization of VEGF in choroidal neovascular membranes in patients affected by AMD. Lopez et al., *Invest. Ophthalmol. Vis. Sci.* 37:855-868 (1996).

Anti-VEGF neutralizing antibodies suppress the growth of a variety of human tumor cell lines in nude mice (Kim et al., *Nature* 362:841-844 (1993); Warren et al., *J. Clin. Invest.* 95:1789-1797 (1995); Borgström et al., *Cancer Res.* 56:4032-4039 (1996); Melnyk et al., *Cancer Res.* 56:921-924 (1996)) and also inhibit intraocular angiogenesis in models of ischemic retinal disorders. Adamis et al., *Arch. Ophthalmol.* 114:66-71 (1996). Therefore, anti-VEGF monoclonal antibodies or other inhibitors of VEGF action are promising candidates for the treatment of tumors and various intraocular neovascular disorders. Such antibodies are described, for example, in EP 817,648 published Jan. 14, 1998; and in WO98/45331 and WO98/45332, both published Oct. 15, 1998. One of the anti-VEGF antibodies, bevacizumab, has been approved by the FDA for use in combination with a chemotherapy regimen to treat metastatic colorectal cancer (CRC). And bevacizumab is being investigated in many ongoing clinical trials for treating various cancer indications.

It is known that extracellular matrix (ECM) plays an important role during the process of angiogenesis. Madri, *Transpl. Immunol.* 5:179-83 (1997). ECs are surrounded by provisional ECM during their migration, and adhere to newly synthesized vascular basement membranes after forming a lumen. In addition to providing a scaffold during capillary morphogenesis, the ECM has been shown to exert complex local controls on the functions of ECs. For example, the ECM is able to regulate the availability of soluble angiogenic mediators to ECs and specify the nature and type of interactions with integrin and cellular adhesion molecules. It has also been suggested that EC survival is regulated by cooperation between growth factor receptors and integrins, which are in turn governed by the composition of the local ECM. Stupack and Cheresh, *Oncogene* 22:9022-29 (2003).

Despite the many advances in the field of angiogenesis, some of the steps during vessel tube formation are still poorly defined. Particularly, little is known about how tubulogenesis is regulated—how vascular cords progress to become tubes, and what factors regulate this transition. In view of the role of angiogenesis in many diseases and disorders, it is desirable to have a means of reducing or inhibiting one or more of the biological effects causing these processes. It is also desirable to have a means of assaying for the presence of pathogenic polypeptides in normal and diseased conditions, and especially cancer. There also exists the need to identify targets and develop means that can enhance the efficacy of existing anti-angiogenesis therapies.

SUMMARY OF THE INVENTION

The present invention is based on the identification and characterization of a novel EC-derived secreted factor, EGF-like domain 7 (EGFL7). EGFL7 is expressed at high levels in the vasculature associated with tissue proliferation, and is down-regulated in most of the mature vessels in normal adult tissues. Loss of EGFL7 function caused significant vascular defects in animal embryos, and reduced tumor growth. Based on its structure, expression and activity, EGFL7 is considered a novel ECM molecule. Furthermore, EGFL7 is found to support EC adhesion and migration, and is implicated in playing a supporting role to angiogenic factors in tumor angiogenesis. EGFL7 antagonists, on the other hand, were found to effectively block EGFL7-associated EC adhesion and migration. Accordingly, the present invention provides novel compositions and uses thereof for modulating (e.g., promoting or inhibiting) processes involved in angiogenesis.

In one embodiment, the present invention provides a composition comprising an EGFL7 antagonist in admixture with a pharmaceutically acceptable carrier. In one aspect, the composition comprises a therapeutically effective amount of the antagonist. In another aspect, the composition comprises a further active ingredient, for example, an anti-angiogenic agent. Preferably, the composition is sterile. The EGFL7 antagonist may be administered in the form of a liquid pharmaceutical formulation, which may be preserved to achieve extended storage stability. Preserved liquid pharmaceutical formulations might contain multiple doses of EGFL7 antagonist, and might, therefore, be suitable for repeated use. In a preferred embodiment, where the composition comprises an antibody, the antibody is a monoclonal antibody, an antibody fragment, a humanized antibody, or a single-chain antibody.

In another embodiment, the present invention provides a method for preparing such a composition useful for the treatment of an angiogenesis associated disorder comprising admixing a therapeutically effective amount of an EGFL7 antagonist with a pharmaceutically acceptable carrier.

In a still further aspect, the present invention provides an article of manufacture comprising:
(a) a composition of matter comprising an EGFL7 antagonist;
(b) a container containing said composition; and
(c) a label affixed to said container, or a package insert included in said container referring to the use of said EGFL7 antagonist in the treatment of an angiogenesis associated disorder, wherein the antagonist may be an antibody which binds to the EGFL7 and blocks its activity. The composition may comprise a therapeutically effective amount of the EGFL7 antagonist.

In another embodiment, the invention provides a method for identifying a compound that inhibits the activity of an EGFL7 polypeptide comprising contacting a test compound with an EGFL7 polypeptide under conditions and for a time sufficient to allow the test compound and polypeptide to interact and determining whether the activity of the EGFL7 polypeptide is inhibited. In a specific preferred aspect, either the test compound or the EGFL7 polypeptide is immobilized on a solid support. In another preferred aspect, the non-immobilized component carries a detectable label. In a preferred aspect, this method comprises the steps of:
(a) contacting cells and a test compound to be screened in the presence of an EGFL7 polypeptide under conditions suitable for the induction of a cellular response normally induced by an EGFL7 polypeptide; and
(b) determining the induction of said cellular response to determine if the test compound is an effective antagonist.

In another preferred aspect, this process comprises the steps of:
(a) contacting cells and a test compound to be screened in the presence of an EGFL7 polypeptide under conditions suitable for the stimulation of cell proliferation by an EGFL7 polypeptide; and
(b) measuring the proliferation of the cells to determine if the test compound is an effective antagonist.

One type of antagonist of an EGFL7 polypeptide that inhibits one or more of the functions or activities of the EGFL7 polypeptide is an antibody. Hence, in another aspect, the invention provides an isolated antibody that binds an EGFL7 polypeptide. In a preferred aspect, the antibody is a monoclonal antibody, which preferably has non-human complementarity-determining-region (CDR) residues and human framework-region (FR) residues. The antibody may be labeled and may be immobilized on a solid support. In a further aspect, the antibody is an antibody fragment, a single-chain antibody, a humanized antibody, or a human antibody. Preferably, the antibody specifically binds to the polypeptide.

In a still further aspect, the invention provides a method of diagnosing a cardiovascular, endothelial or angiogenic disorder in a mammal which comprises analyzing the level of expression of a gene encoding an EGFL7 polypeptide (a) in a test sample of tissue cells obtained from said mammal, and (b) in a control sample of known normal tissue cells of the same cell type, wherein a higher or lower expression level in the test sample as compared to the control sample is indicative of the presence of a cardiovascular, endothelial or angiogenic disorder in said mammal. The expression of a gene encoding an EGFL7 polypeptide may optionally be accomplished by measuring the level of mRNA or the polypeptide in the test sample as compared to the control sample.

In a still further aspect, the present invention provides a method of diagnosing a cardiovascular, endothelial or angiogenic disorder in a mammal which comprises detecting the presence or absence of an EGFL7 polypeptide in a test sample of tissue cells obtained from said mammal, wherein the presence or absence of said EGFL7 polypeptide in said test sample is indicative of the presence of a cardiovascular, endothelial or angiogenic disorder in said mammal.

In a still further embodiment, the invention provides a method of diagnosing a cardiovascular, endothelial or angiogenic disorder in a mammal comprising (a) contacting an anti-EGFL7 antibody with a test sample of tissue cells obtained from the mammal, and (b) detecting the formation of a complex between the antibody and the EGFL7 polypeptide in the test sample, wherein the formation of said complex is indicative of the presence of a cardiovascular, endothelial or angiogenic disorder in the mammal. The detection may be qualitative or quantitative, and may be performed in comparison with monitoring the complex formation in a control sample of known normal tissue cells of the same cell type. A larger or smaller quantity of complexes formed in the test sample indicates the presence of a cardiovascular, endothelial or angiogenic dysfunction in the mammal from which the test tissue cells were obtained. The antibody preferably carries a detectable label. Complex formation can be monitored, for example, by light microscopy, flow cytometry, fluorimetry, or other techniques known in the art. The test sample is usually obtained from an individual suspected to have a cardiovascular, endothelial or angiogenic disorder.

In another embodiment, the invention provides a method for determining the presence of an EGFL7 polypeptide in a sample comprising exposing a sample suspected of containing the EGFL7 polypeptide to an anti-EGFL7 antibody and determining binding of said antibody to a component of said sample. In a specific aspect, the sample comprises a cell suspected of containing the EGFL7 polypeptide and the antibody binds to the cell. The antibody is preferably detectably labeled and/or bound to a solid support.

In further aspects, the invention provides a cardiovascular, endothelial or angiogenic disorder diagnostic kit comprising an anti-EGFL7 antibody and a carrier in suitable packaging. Preferably, such kit further comprises instructions for using said antibody to detect the presence of the EGFL7 polypeptide. Preferably, the carrier is a buffer, for example. Preferably, the cardiovascular, endothelial or angiogenic disorder is cancer.

In yet another embodiment, the present invention provides a method of reducing or inhibiting angiogenesis in a subject having a pathological condition associated with angiogenesis, comprising administering to the subject an EGFL7 antagonist capable of interfering with EGFL7-induced endothelial cell migration, thereby reducing or inhibiting angiogenesis in the subject. Preferably the EGFL7 antagonist is an anti-EGFL7 antibody. The antagonist's ability to interfere with EGFL7-induced EC migration can be detected, for example, in an in vitro cell migration assay.

In one preferred embodiment, the pathological condition associated with angiogenesis is a cancer. In another preferred embodiment, the pathological condition associated with angiogenesis is an intraocular neovascular disease. In yet another preferred embodiment, the EGFL7 antagonist is co-administered with another anti-angiogenic agent, such as an anti-VEGF antibody including bevacizumab. The present invention also provides a method of enhancing the efficacy of an anti-angiogenic agent treatment in a subject having a pathological condition associated with angiogenesis, comprising administering to the subject an EGFL7 antagonist in combination with the anti-angiogenic agent. Such a method will be useful in treating cancers or intraocular neovascular diseases, especially those diseases or stages of the diseases that responded poorly to a treatment with the anti-angiogenic agent alone. The anti-angiogenic agent can be any agent capable of reducing or inhibiting angiogenesis, including VEGF antagonists such as anti-VEGF antibody. When treating tumor, the EGFL7 antagonist alone or in combination with an anti-angiogenic agent can be further combined with a chemotherapy regime comprising one or more chemotherapeutic agents. Radioactive therapy can also be combined for enhanced efficacy.

In yet another embodiment, the invention provides a method for promoting vascular formation in a mammal comprising administering to the mammal an EGFL7 polypeptide or an agonist of an EGFL7 polypeptide, wherein vascular formation in said mammal is stimulated. Preferably, the mammal is human.

In yet another embodiment, the invention provides a method for stimulating angiogenesis in a mammal comprising administering a therapeutically effective amount of an EGFL7 polypeptide or agonist thereof to the mammal. Preferably, the mammal is a human, and more preferably angiogenesis would promote tissue regeneration or wound healing.

In yet another embodiment, the invention provides a method for modulating (e.g., inhibiting or stimulating) vascular tube formation in a mammal comprising administering to the mammal a composition comprising an EGFL7 polypeptide, agonist or antagonist thereof.

In yet another embodiment, the invention provides a method for modulating (e.g., inducing or reducing) angiogenesis by modulating (e.g., inducing or reducing) endothelial cell migration in a mammal comprising administering to the mammal an EGFL7 polypeptide, agonist or antagonist thereof, wherein endothelial cell migration in said mammal is modulated.

BRIEF DESCRIPTION OF THE DRAWINGS

FIGS. 1a and 1b show that EGFL7 is conserved during vertebrate evolution. a: Amino acid alignment among human, mouse, *xenopus* and zebrafish EGFL7s. The EGFL7 gene encodes a putative secreted protein of ~30 kD. The human (*Homo sapiens*) amino acid sequence shares 77.45%, 47.14% and 42.96% homology to that of the mouse (*Mus musculus*), frog (*Xenopus laevis*) and zebrafish (*Danio rerio*), respectively. Structural analysis using a number of algorithms predicts that the EGFL7 proteins contain the following domains (in boxes starting from the N'-terminus): a signal sequence, an EMI domain a, two EGF-like domains in the central portion, followed by a leucine and valine rich C-terminal region. b: Zebrafish EGFL7 cDNA, amino acid, and an intron sequence. Arrowed lines indicate the two antisense oligos, $AS_{-47}$ and $AS_{195}$, and the PCR primers used to detect intron retention.

FIGS. 3a-3d show that EGFL7 gene knockdown causes vascular tubulogenesis defect in zebrafish embryos. Zebrafish embryos injected with control ($Con_{-47}$ or $Con_{195}$) or EGFL7antisense ($AS_{-47}$ or $AS_{195}$) oligos. a: Gross morphology at 48 hpf. Arrow points to pericardial edema, arrowhead indicates hemorrhage. b-d:fli1 expression at 23 hpf (b) and 30 hpf (c-d). d: Close up view of the mid trunk vasculatures boxed in c. White arrowhead: lumen of the dorsal aorta, black arrowhead: lumen of the posterior cardinal vein, black arrow: intersegmental vessels. Scale bar: 0.6 mm (a), 0.23 mm (d) and 0.5 mm (b, c).

FIGS. 4a-4h depict that EC number is unaltered in the EGFL7 KDs. flk1:GFP transgenic fish injected with control (a, c, e, g) or antisense (b, d, f, h) oligos were analyzed at 22-somite (a-d) or 30 hpf (e-h). a, b: Dorsal view. e, f: Lateral view. c, d, g, h: Cross sections taken at the level indicated by white-lines in a-b, e-f were counter stained with phalloidin and DAPI. PD: pronephric ducts, So: somites, N: Notochords, white arrows: arterial ECs, white arrowheads=venous ECs, DA=dorsal aorta, PCV=posterior cardinal vein. Scale bar: 0.33 mm (a, b), 0.03 mm (c, d, g, h), 0.47 mm (e, f).

FIGS. 5a-5g show that EGFL7 promotes EC adhesion. Vinculin staining of human umbilical-cord vascular endothelial cells (HUVEC) reveals focal adhesion formation on fibronectin (b), type I collagen (c), and EGFL7 (d), but not BSA (a). Adhesion strength on EGFL7 is weaker than on collagen or fibronectin since fewer cells remain adherent to the EGFL7 substrate after spinning at 46 g (e). Dose-dependent blockage of HUVEC adhesion to EGFL7 but not fibronectin by an anti-EGFL7 antibody confirms substrate specificity. A control antibody (anti-B7x) has no effect on any substrate (f). g: Kinetics of HUVEC adhesion on various substrates. Scale bar: 0.03 mm (a-d).

Figure 6:
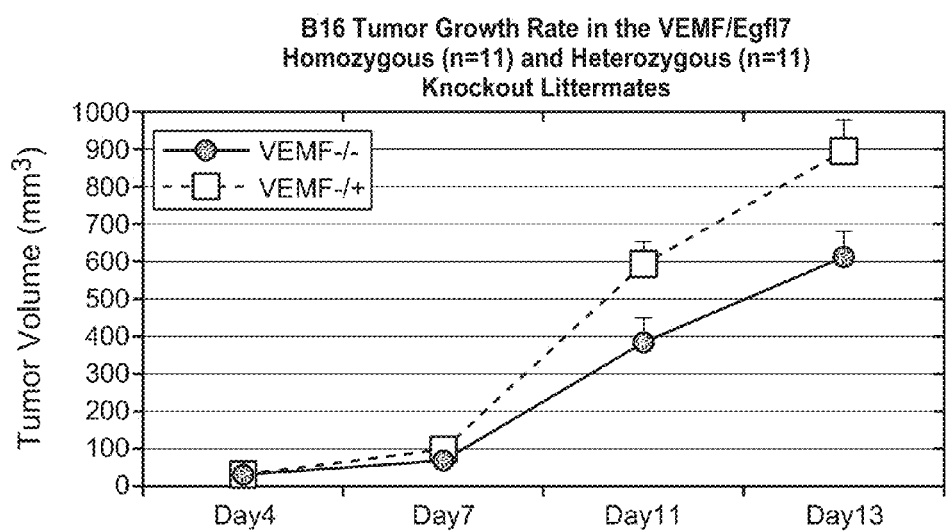

FIG. 6 depicts comparison of B16 melanoma tumor growth rates in the EGFL7$^{-/-}$ homozygous (n=11) and the EGFL7$^{+/-}$ heterozygous (n=11) knockout mice.

Figure 7A:
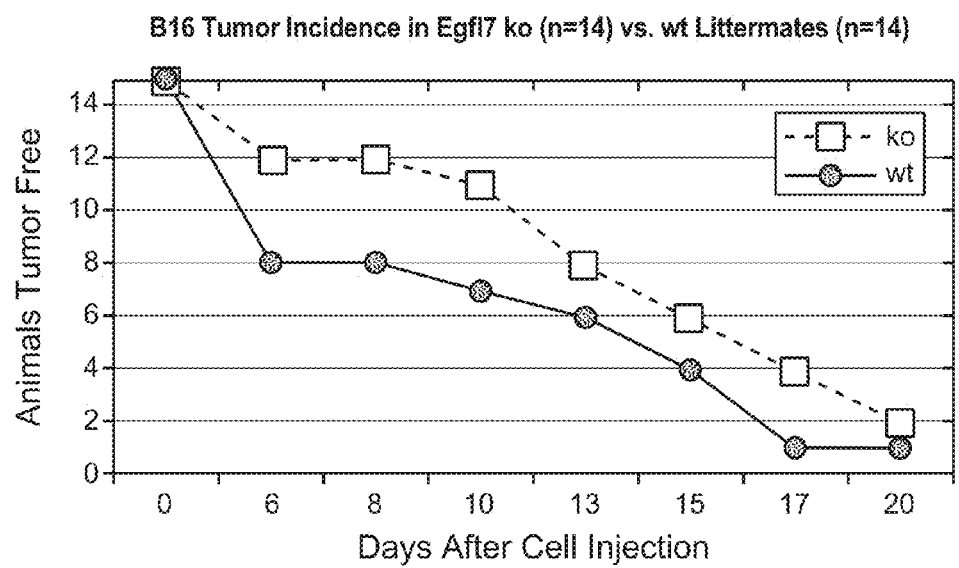
Figure 7B:
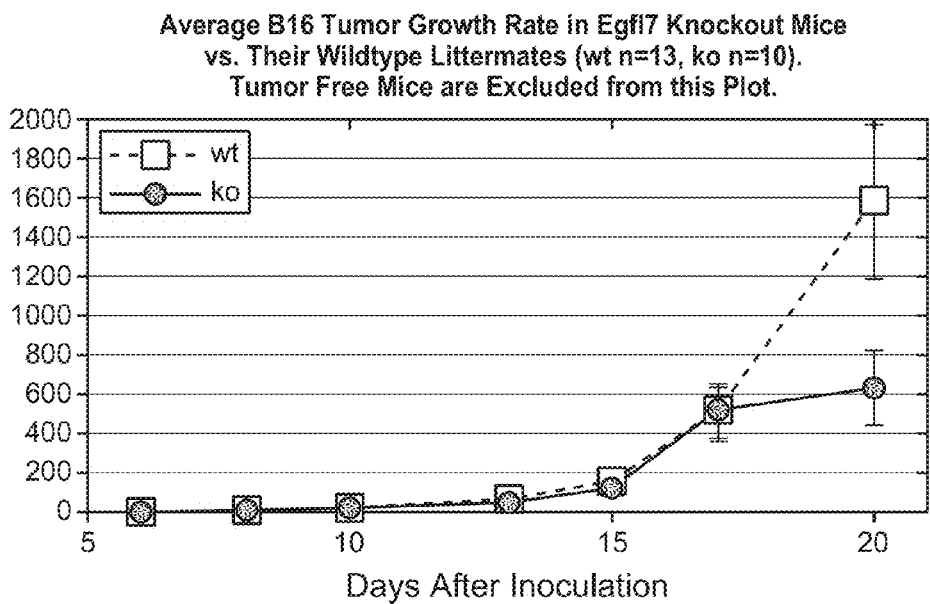

FIGS. 7a-7b depict comparisons of B16 melanoma tumor incidence and growth rate in the EGFLT$^{-/-}$ homozygous knockout mice (n=10) versus their wildtype littermates (n=13). In 7b, tumor free mice were excluded.

DETAILED DESCRIPTION OF THE PREFERRED EMBODIMENTS

Definitions

Unless defined otherwise, technical and scientific terms used herein have the same meaning as commonly understood by one of ordinary skill in the art to which this invention belongs. See, e.g. Singleton et al., *Dictionary of Microbiology and Molecular Biology* 2nd ed., J. Wiley & Sons (New York, N.Y. 1994); Sambrook et al., *Molecular Cloning, A Laboratory Manual*, Cold Springs Harbor Press (Cold Springs Harbor, N.Y. 1989). For purposes of the present invention, the following terms are defined below.

As used herein, the terms "EGFL7" and "EGFL7 polypeptide," which are used interchangeably, refer to native sequence EGFL7, EGFL7 variants, and chimeric EGFL7, each of which is defined herein. Optionally, the EGFL7 is not associated with native glycosylation. "Native glycosylation" refers to the carbohydrate moieties that are covalently attached to EGFL7 when it is produced in mammalian cells, particularly in the cells in which it is produced in nature. Accordingly, human EGFL7 produced in a non-human cell is an example of EGFL7 that may "not be associated with native glycosylation." Sometimes the EGFL7 may not be glycosylated at all, as in the case where it is produced in prokaryotes, e.g. *E. coli*.

EGFL7 nucleic acid is RNA or DNA that encodes an EGFL7 polypeptide, as defined above, or which hybridizes to such DNA or RNA and remains stably bound to it under stringent hybridization conditions and is greater than about 10 nucleotides in length. Stringent conditions are those which (1) employ low ionic strength and high temperature for washing, for example, 0.15 M NaCl/0.015 M sodium citrate/0.1% NaDodSO$_4$ at 50° C., or (2) use during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.

Nucleic acid is operably linked when it is placed into a functional relationship with another nucleic acid sequence. EGFL7 nucleic acid may be operably linked with another nucleic acid sequence in a vector such that it may be expressed in a particular host organism. This may be done by methods well known in the art. For example, DNA for a presequence or a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adapters or linkers are used in accord with conventional practice.

Figure 1A:
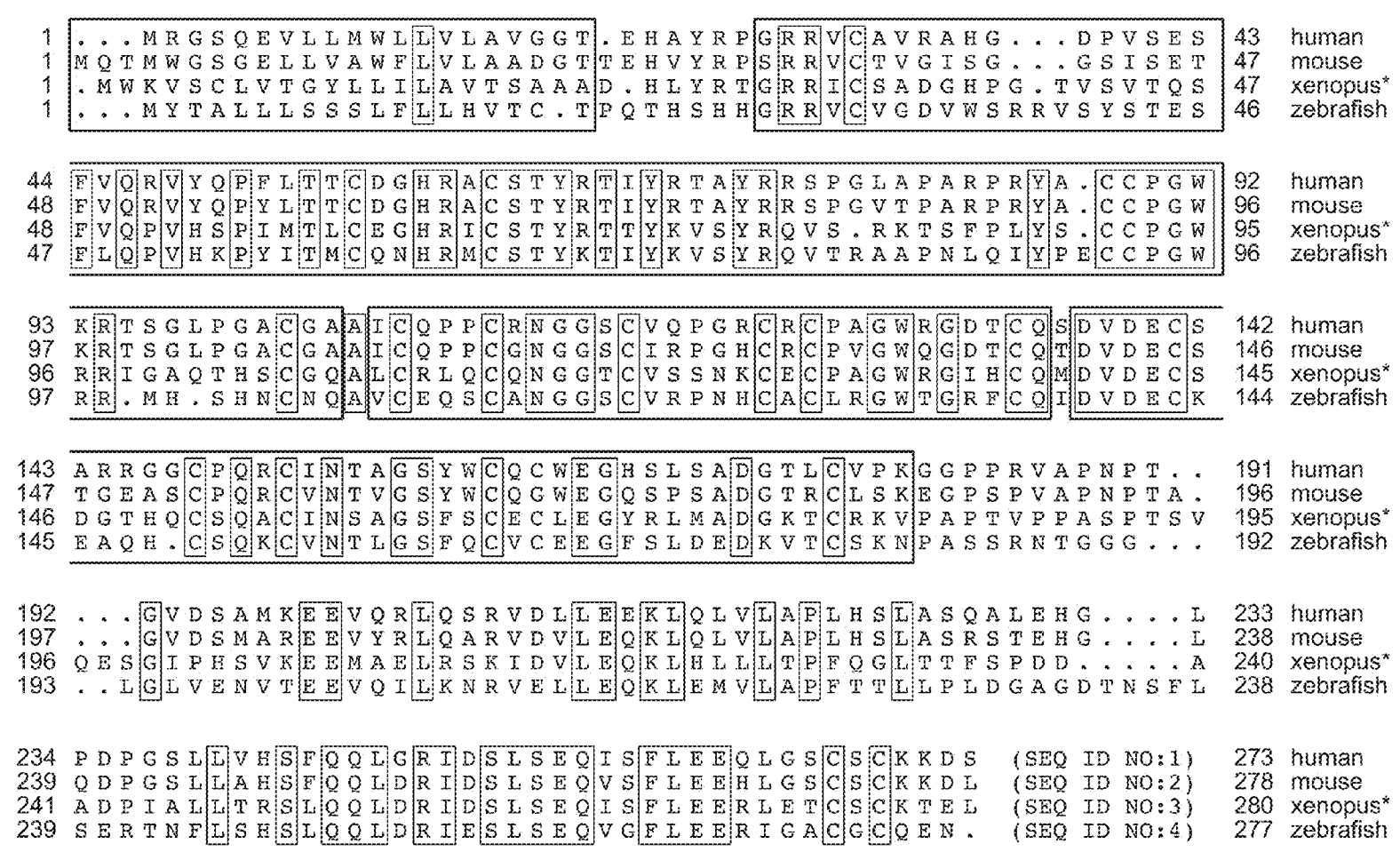

"Native sequence EGFL7" comprises a polypeptide having the same amino acid sequence as EGFL7 derived from nature, regardless of its mode of preparation or species. Thus, native sequence EGFL7 can have the amino acid sequence of naturally occurring human EGFL7, murine EGFL7, *Xenopus* EGFL7, zebrafish EGFL7 or EGFL7 from any other species. For example a preferred full-length native sequence human EGFL7 amino acid sequence is shown in FIG. 1A (SEQ ID NO: 1). A native sequence mouse EGFL7 amino acid sequence is shown in FIG. 1A (SEQ ID NO: 2). Such native sequence EGFL7 can be isolated from nature or can be produced by recombinant and/or synthetic means. The term "native sequence EGFL7" specifically encompasses naturally occurring prepro, pro and mature forms and truncated forms of EGFL7, naturally occurring variant forms, and naturally occurring allelic variants.

"EGFL7 variants" are biologically active EGFL7 polypeptides having an amino acid sequence which differs from the sequence of a native sequence EGFL7 polypeptide, such as those shown in FIG. 1A (SEQ ID NOs:1-4) for human, murine, *Xenopus* and zebrafish EGFL7 respectively, by virtue of an insertion, deletion, modification and/or substitution of one or more amino acid residues within the native sequence. EGFL7 variants generally have less than 100% sequence identity with a native sequence EGFL7, such as the human EGFL7 of SEQ ID NO: 1. Ordinarily, however, a biologically active EGFL7 variant will have an amino acid sequence with at least about 70% amino acid sequence identity with the amino acid sequence of a naturally occurring EGFL7 such as the human EGFL7 of SEQ ID NO: 1, preferably at least about 75%, more preferably at least about 80%, even more preferably at least about 85%, even more preferably at least about 90%, with increasing preference of at least about 95% to at least about 99% amino acid sequence identity, in 1% increments. The EGFL7 variants include peptide fragments of at least 5 amino acids that retain a biological activity of the corresponding native sequence EGFL7 polypeptide. EGFL7 variants also include EGFL7 polypeptides wherein one or more amino acid residues are added at the N- or C-terminus of, or within, a native EGFL7 sequence. EGFL7 variants also include EGFL7 polypeptides where a number of amino acid residues are deleted and optionally substituted by one or more amino acid residues. EGFL7 variants also may be covalently modified, for example by substitution with a moiety other than a naturally occurring amino acid or by modifying an amino acid residue to produce a non-naturally occurring amino acid. EGFL7 variants may comprise a heparin binding domain.

"Percent amino acid sequence identity" with respect to the EGFL7 sequence is defined herein as the percentage of amino acid residues in the candidate sequence that are identical with the residues in the EGFL7 sequence, after aligning the sequences and introducing gaps, if necessary, to achieve the maximum percent sequence identity, and not considering any conservative substitutions as part of the sequence identity. None of N-terminal, C-terminal, or internal extensions, deletions or insertions into the candidate EGFL7 sequence shall be construed as affecting sequence identity or homology. Methods and computer programs for the alignment are well known in the art. One such computer program is "ALIGN-2," authored by Genentech, which has been filed with user documentation in the United States Copyright Office, Washington, D.C. 20559, where it is registered under U.S. Copyright Registration No. TXU510087.

A "chimeric EGFL7" molecule is a polypeptide comprising full-length EGFL7 or one or more domains thereof fused or bonded to heterologous polypeptide. The chimeric EGFL7 molecule will generally share at least one biological property in common with naturally occurring EGFL7. An example of a chimeric EGFL7 molecule is one that is epitope tagged for purification purposes. Another chimeric EGFL7 molecule is an EGFL7 immunoadhesin.

"Isolated EGFL7" means EGFL7 that has been purified from an EGFL7 source or has been prepared by recombinant or synthetic methods and purified. Purified EGFL7 is substantially free of other polypeptides or peptides. "Substantially free" here means less than about 5%, preferably less than about 2%, more preferably less than about 1%, even more preferably less than about 0.5%, most preferably less than about 0.1% contamination with other source proteins.

"Essentially pure" protein means a composition comprising at least about 90% by weight of the protein, based on total weight of the composition, preferably at least about 95% by weight, more preferably at least about 90% by weight, even more preferably at least about 95% by weight. "Essentially homogeneous" protein means a composition comprising at least about 99% by weight of protein, based on total weight of the composition.

The term "antagonist" is used in the broadest sense, and includes any molecule that partially or fully blocks, inhibits, or neutralizes a biological activity of a native EGFL7 polypeptide. Suitable antagonist molecules specifically include antagonist antibodies or antibody fragments, fragments or amino acid sequence variants of native EGFL7 polypeptides, peptides, soluble fragments of EGFL7 receptor(s), small organic molecules, etc. Methods for identifying agonists or antagonists of an EGFL7 polypeptide may comprise contacting an EGFL7 polypeptide with a candidate agonist or antagonist molecule and measuring a detectable change in one or more biological activities normally associated with the EGFL7 polypeptide.

"Active" or "activity" for the purposes herein refers to form(s) of EGFL7 which retain a biological and/or an immunological activity of native or naturally-occurring EGFL7, wherein "biological" activity refers to a biological function (either inhibitory or stimulatory) caused by a native or naturally-occurring EGFL7 other than the ability to induce the production of an antibody against an antigenic epitope possessed by a native or naturally-occurring EGFL7 and an "immunological" activity refers to the ability to induce the production of an antibody against an antigenic epitope possessed by a native or naturally-occurring EGFL7.

Thus, "biologically active" when used in conjunction with "EGFL7" or "isolated EGFL7" or an agonist of EGFL7, means an EGFL7 polypeptide that exhibits or shares an effector function of native sequence EGFL7. A principal effector function of EGFL7 is its ability to promote vascular formation. Even more preferably, the biological activity is the ability to regulate tubulogenesis.

"EGFL7 receptor" is a molecule to which EGFL7 binds and which mediates the biological properties of EGFL7.

The term "antibody" herein is used in the broadest sense and specifically covers human, non-human (e.g. murine) and humanized monoclonal antibodies (including full length monoclonal antibodies), polyclonal antibodies, multispecific antibodies (e.g., bispecific antibodies), and antibody fragments so long as they exhibit the desired biological activity.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3 and FR4, respectively), largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, *J. Mol. Biol.* 196:901-917 (1987)). "Framework" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment that contains a complete antigen-recognition and -binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa ($\kappa$) and lambda ($\lambda$), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The heavy-chain constant domains that correspond to the different classes of immunoglobulins are called $\alpha$, $\delta$, $\epsilon$, $\gamma$, and $\mu$, respectively. The subunit structures and three-dimensional configurations of different classes of immunoglobulins are well known.

"Antibody fragments" comprise a portion of a full-length antibody, generally the antigen binding or variable domain thereof. Examples of antibody fragments include Fab, Fab', F(ab')$_2$, and Fv fragments; diabodies; linear antibodies; single-chain antibody molecules; and multi-specific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al. *Nature* 321:522-525 (1986); Reichmann et al. *Nature* 332:323-329 (1988); and Presta *Curr. Op. Struct. Biol.* 2:593-596 (1992).

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. *Proc. Natl. Acad. Sci. USA* 90:6444-6448 (1993).

The expression "linear antibodies" when used throughout this application refers to the antibodies described in Zapata et al. *Protein Eng.* 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

The term "epitope" is used to refer to binding sites for (monoclonal or polyclonal) antibodies on protein antigens.

By "agonist antibody" is meant an antibody that is an EGFL7 agonist and thus possesses one or more of the biological properties of native sequence EGFL7.

The term "EGFL7 immunoadhesin" is used interchangeably with the term "EGFL7-immunoglobulin chimera", and refers to a chimeric molecule that combines at least a portion of an EGFL7 molecule (native or variant) with an immunoglobulin sequence. The immunoglobulin sequence preferably, but not necessarily, is an immunoglobulin constant domain. Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use.

Examples of homomultimeric immunoadhesins which have been described for therapeutic use include the CD4-IgG immunoadhesin for blocking the binding of HIV to cell-surface CD4. Data obtained from Phase I clinical trials, in which CD4-IgG was administered to pregnant women just before delivery, suggests that this immunoadhesin may be useful in the prevention of maternal-fetal transfer of HIV (Ashkenazi et al., *Intern. Rev. Immunol.* 10:219-227 (1993)). An immunoadhesin which binds tumor necrosis factor (TNF) has also been developed. TNF is a proinflammatory cytokine which has been shown to be a major mediator of septic shock. Based on a mouse model of septic shock, a TNF receptor immunoadhesin has shown promise as a candidate for clinical use in treating septic shock (Ashkenazi, A. et al. *PNAS USA* 88:10535-10539 (1991)). ENBREL® (etanercept), an immunoadhesin comprising a TNF receptor sequence fused to an IgG Fc region, was approved by the U.S. Food and Drug Administration (FDA), on Nov. 2, 1998, for the treatment of rheumatoid arthritis. The new expanded use of ENBREL® in the treatment of rheumatoid arthritis was approved by FDA on Jun. 6, 2000. For recent information on TNF blockers, including ENBREL®, see Lovell et al., *N. Engl. J. Med.* 342:763-169 (2000), and accompanying editorial on p 810-811; and Weinblatt et al., *N. Engl. J. Med.* 340:253-259 (1999); reviewed in Maini and Taylor, *Annu. Rev. Med.* 51:207-229 (2000).

If the two arms of the immunoadhesin structure have different specificities, the immunoadhesin is called a "bispecific immunoadhesin" by analogy to bispecific antibodies. Dietsch et al., *J. Immunol. Methods* 162:123 (1993) describe such a bispecific immunoadhesin combining the extracellular domains of the adhesion molecules, E-selectin and P-selectin, each of which selectins is expressed in a different cell type in nature. Binding studies indicated that the bispecific immunoglobulin fusion protein so formed had an enhanced ability to bind to a myeloid cell line compared to the monospecific immunoadhesins from which it was derived.

The term "heteroadhesin" is used interchangeably with the expression "chimeric heteromultimer adhesin" and refers to a complex of chimeric molecules (amino acid sequences) in which each chimeric molecule combines a biologically active portion, such as the extracellular domain of each of the heteromultimeric receptor monomers, with a multimerization domain. The "multimerization domain" promotes stable interaction of the chimeric molecules within the heteromultimer complex. The multimerization domains may interact via an immunoglobulin sequence, leucine zipper, a hydrophobic region, a hydrophilic region, or a free thiol that forms an intermolecular disulfide bond between the chimeric molecules of the chimeric heteromultimer. The multimerization domain may comprise an immunoglobulin constant region. In addition a multimerization region may be engineered such that steric interactions not only promote stable interaction, but further promote the formation of heterodimers over homodimers from a mixture of monomers. "Protuberances" are constructed by replacing small amino acid side chains from the interface of the first polypeptide with larger side chains (e.g. tyrosine or tryptophan). Compensatory "cavities" of identical or similar size to the protuberances are optionally created on the interface of the second polypeptide by replacing large amino acid side chains with smaller ones (e.g. alanine or threonine). The immunoglobulin sequence preferably, but not necessarily, is an immunoglobulin constant domain. The immunoglobulin moiety in the chimeras of the present invention may be obtained from $IgG_1$, $IgG_2$, $IgG_3$ or $IgG_4$ subtypes, IgA, IgE, IgD or IgM, but preferably $IgG_1$ or $IgG_3$.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. Specifically, the treatment may directly prevent, slow down or otherwise decrease the pathology of cellular degeneration or damage, such as the pathology of tumor cells in cancer treatment, or may render the cells more susceptible to treatment by other therapeutic agents.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, other higher primates, domestic and farm animals, and zoo, sports, or pet animals, such as dogs, cats, cattle, horses, sheep, pigs, goats, rabbits, etc. Preferably, the mammal is human.

"Tumor", as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1 (see, e.g., Agnew, Chem. Intl. Ed. Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-nor-leucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON•toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

An "intraocular neovascular disease" is a disease characterized by ocular neovascularization. Examples of intraocular neovascular diseases include, but are not limited to, proliferative retinopathies, choroidal neovascularization (CNV), age-related macular degeneration (AMD), diabetic and other ischemia-related retinopathies, diabetic macular edema, pathological myopia, von Hippel-Lindau disease, histoplasmosis of the eye, Central Retinal Vein Occlusion (CRVO), corneal neovascularization, retinal neovascularization, etc.

The "pathology" of a disease includes all phenomena that compromise the well-being of the patient. For cancer, this includes, without limitation, abnormal or uncontrollable cell growth, metastasis, interference with the normal functioning of neighboring cells, release of cytokines or other secretory products at abnormal levels, suppression or aggravation of inflammatory or immunological response, etc.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

A "liposome" is a small vesicle composed of various types of lipids, phospholipids and/or surfactant which is useful for delivery of a drug (such as an EGFL7 polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

The terms "vascular endothelial growth factor", "VEGF", "VEGF polypeptide" and "VEGF protein" when used herein encompass native sequence VEGF and VEGF variants (which are further defined herein). The VEGF polypeptide may be isolated from a variety of sources, such as from human tissue types or from another source, or prepared by recombinant and/or synthetic methods.

A "native sequence VEGF" comprises a polypeptide having the same amino acid sequence as a VEGF derived from nature. Such native sequence VEGF can be isolated from nature or can be produced by recombinant and/or synthetic means. The term "native sequence VEGF" specifically encompasses naturally-occurring truncated or secreted forms (e.g., an extracellular domain sequence), naturally-occurring variant forms (e.g., alternatively spliced forms) and naturally-occurring allelic variants of the VEGF. In one embodiment of the invention, the native sequence VEGF is one of the five known isoforms, consisting of 121, 145, 165, 189, and 206 amino acid residues, respectively, as described, for example in U.S. Pat. Nos. 5,332,671 and 5,240,848; in PCT Publication No. WO 98/10071; Leung et al., *Science* 246:1306-1309 (1989); and Keck et al., *Science* 246:1309-1312 (1989).

"VEGF variant polypeptide" means an active VEGF polypeptide as defined below having at least about 80%, preferably at least about 85%, more preferably at least about 90%, event more preferably at least about 95%, most preferably at least about 98% amino acid sequence identity with the amino acid sequence of a native sequence VEGF. Such VEGF variant polypeptides include, for instance, VEGF polypeptides wherein one or more amino acid residues are added, or deleted, at the N- and/or C-terminus, as well as within one or more internal domains, of the native sequence.

The sequence identity (either amino acid or nucleic acid) for VEGF is determined using the same approach specifically described with regard to EGFL7. Similarly, the definitions provided for agonist and antagonists of EGFL7, including but not limited to antibodies, will apply to VEGF agonists and antagonists.

Methods for Carrying out the Invention

EGFL7

The EGFL7 gene encodes a secreted, ECM associated protein of ~30 kD that is evolutionarily conserved. The human (*homo sapiens*) amino acid sequence (SEQ ID NO:1) shares about 77%, 47% and 43% homology to that of the mouse (*Mus musculus*; SEQ ID NO:2), frog (*Xenopus laevis*; SEQ ID NO:3) and zebrafish (*Danio rerio*; SEQ ID NO:4), respectively. The EGFL7 protein contains a signal sequence, an EMI domain at the N-terminus (EMI domain is present in a number of extracellular matrix associated proteins involved in regulating cell adhesion), followed by two EGF-like domains and a leucine and valine rich C-terminal region.

Nucleic acid and polypeptide molecules are used in the present invention. The human, mouse, *xenopus* and zebrafish EGFL7 amino acid sequences are provided as SEQ ID NOs: 1-4, respectively (see FIG. 1A). The zebrafish cDNA (with partial genomic intron sequence) is provided as SEQ ID NO:5 (see FIG. 1B). The polynucleotides used in the present invention can be obtained using standard techniques well known to those skilled in the art such as, for example, hybridization screening and PCR methodology.

Accession numbers for EGFL7 are: NM_016215 (*homo sapiens* EGFL7/VE-statin), NM_178444 (*mus musculus* EGFL7), AF184973 (*mus musculus* Notch4-like), P_AAZ37135 (*mus musculus* TANGO125), BC044267 (*xenopus laevis* NEU1). AY542170 (*danio rerio* EGFL7). Egfl8 accession numbers are: NM_030652 (*Homo Sapiens*), NM_152922 (*mus musculus*).

Preparation and Identification of Modulators of EGFL7 Activity

The present invention also encompasses methods of screening compounds to identify those that mimic or enhance one or more biological activity of EGFL7 (agonists); or inhibit or reduce the effect of EGFL7 (antagonists). EGFL7 agonists and antagonists are also referred to as EGFL7 modulators. Screening assays for antagonist drug candidates are designed to identify compounds that bind or complex with EGFL7 polypeptides, or otherwise interfere with the interaction of EGFL7 with other cellular proteins.

Small Molecule Screening

Small molecules may have the ability to act as EGFL7 agonists or antagonists and thus to be therapeutically useful. Such small molecules may include naturally occurring small molecules, synthetic organic or inorganic compounds and peptides. However, small molecules in the present invention are not limited to these forms. Extensive libraries of small molecules are commercially available and a wide variety of assays are well known in the art to screen these molecules for the desired activity.

Candidate EGFL7 agonist or antagonist small molecules are preferably identified first in an assay that allows for the rapid identification of potential modulators of EGFL7 activity. An example of such an assay is a protein-protein binding assay wherein the ability of the candidate molecule to bind to an EGFL7 receptor is measured. In another example, the ability of candidate molecules to interfere with EGFL7 binding to an EGFL7 receptor is measured.

In a preferred embodiment, small molecule EGFL7 agonists are identified by their ability to mimic one or more of the biological activities of EGFL7. For example, small molecules are screened for their ability to induce proliferation of endothelial cells, to promote endothelial cell survival, as described in examples 2 and 3 below or to induce angiogenesis, as described in example 4 below.

In another embodiment, small molecule EGFL7 antagonists are identified by their ability to inhibit one or more of the biological activities of EGFL7. Thus a candidate compound is contacted with EGFL7. The biological activity of the EGFL7 is then assessed. In one embodiment the ability of the EGFL7 to stimulate endothelial cell proliferation is determined, for example as described in Example 2. In another embodiment the ability of the EGFL7 to promote endothelial cell survival is determined, for example as described in Example 3. A compound is identified as an antagonist where the biological activity of EGFL7 is inhibited.

Compounds identified as EGFL7 agonists or antagonists may be used in the methods of the present invention. For example, EGFL7 antagonists may be used to treat cancer.

Screening Assays for Proteins that Interact with EGFL7

Any method suitable for detecting protein-protein interactions may be employed for identifying proteins or other molecules, including but not limited to transmembrane or intracellular proteins, that interact with EGFL7. Among the traditional methods that may be employed are co-immunoprecipitation, crosslinking and co-purification through gradients or chromatographic columns to identify proteins that interact with EGFL7. For such assays, the EGFL7 component can be a full-length protein, a soluble derivative thereof, a peptide corresponding to a domain of interest, or a fusion protein containing some region of EGFL7.

Methods may be employed which result in the simultaneous identification of genes that encode proteins capable of interacting with EGFL7. These methods include, for example, probing expression libraries, in a manner similar to the well-known technique of antibody probing of λgt11 libraries, using labeled EGFL7 or a variant thereof.

A method that detects protein interactions in vivo, the two-hybrid system, is described in detail for illustration only and not by way of limitation. One version of this system has been described (Chien et al., *Proc. Natl. Acad. Sci. USA* 88:9578-9582 (1991)) and is commercially available from Clontech (Palo Alto, Calif.).

Briefly, utilizing such a system, plasmids are constructed that encode two hybrid proteins: one plasmid consists of nucleotides encoding the DNA-binding domain of a transcription activator protein fused to a nucleotide sequence encoding EGFL7, or a polypeptide, peptide, or fusion protein therefrom, and the other plasmid consists of nucleotides encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, EGFL7 can be used as the bait gene product. Total genomic or cDNA sequences are fused to the DNA encoding an activation domain. This library and a plasmid encoding a hybrid of a bait EGFL7 gene product fused to the DNA-binding domain are cotransformed into a yeast reporter strain, and the resulting transformants are screened for those that express the reporter gene. For example, and not by way of limitation, a bait EGFL7 gene sequence, e.g., the genes open reading frame, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with the bait EGFL7 gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait EGFL7 gene-GAL4 fusion plasmid into a yeast strain that contains a lacZ gene driven by a promoter which contains a GAL4 activation sequence. A cDNA encoded protein, fused to GAL4 transcriptional activation domain, that interacts with the bait EGFL7 gene product will reconstitute an active GAL4 protein and thereby drive expression. Colonies that drive expression can be detected by methods routine in the art. The cDNA can then be purified from these strains, and used to produce and isolate the bait EGFL7 gene-interacting protein using techniques routinely practiced in the art.

Assays for Compounds that Modulate EGFL7 Expression or Activity

The following assays are designed to identify compounds that interact with (e.g., bind to) EGFL7, compounds that interfere with the interaction of EGFL7 with its binding partners, cognate or receptor, and to compounds that modulate the activity of EGFL7 gene expression (i.e., modulate the level of EGFL7 gene expression) or modulate the levels of EGFL7 in the body. Assays may additionally be utilized which identify compounds that bind to EGFL7 gene regulatory sequences (e.g., promoter sequences) and, consequently, may modulate EGFL7 gene expression. See, e.g., Platt, K. A., *J. Biol. Chem.* 269:28558-28562 (1994), which is incorporated herein by reference in its entirety.

The compounds which may be screened in accordance with the invention include, but are not limited to peptides, antibodies and fragments thereof, and other organic compounds (e.g., peptidomimetics) that bind to an EGFL7 or an EGFL7 receptor and either mimic the activity triggered by a natural ligand (i.e., agonists) or inhibit the activity triggered by the natural ligand (i.e., antagonists).

Such compounds may include, but are not limited to, peptides such as, for example, soluble peptides, including but not limited to members of random peptide libraries; (see, e.g., Lam, K. S. et al., *Nature* 354:82-84 (1991); Houghten, R. et al., *Nature* 354:84-86 (1991)), and combinatorial chemistry-derived molecular library made of D- and/or L-configuration amino acids, phosphopeptides (including, but not limited to members of random or partially degenerate, directed phosphopeptide libraries; see, e.g., Songyang, Z. et al., *Cell* 72:767-778 (1993)), antibodies (including, but not limited to, polyclonal, monoclonal, humanized, anti-idiotypic, chimeric or single chain antibodies, and FAb, $F(ab')_2$ and FAb expression library fragments, and epitope-binding fragments thereof), and small organic or inorganic molecules.

Other compounds which can be screened in accordance with the invention include, but are not limited to small organic molecules that are able to gain entry into an appropriate cell (e.g. an endothelial cell) and affect the expression of an EGFL7 gene or some other gene involved in an EGFL7 mediated pathway (e.g., by interacting with the regulatory region or transcription factors involved in gene expression); or such compounds that affect or substitute for the activity of the EGFL7 or the activity of some other intracellular factor involved in an EGFL7 signal transduction, catabolic, or metabolic pathways.

Computer modeling and searching technologies permit identification of compounds, or the improvement of already identified compounds, that can modulate EGFL7 expression or activity. Having identified such a compound or composition, the active sites or regions are identified. Such active sites might typically be ligand binding sites. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intramolecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site (or binding site), either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential modulators of EGFL7 activity.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites (or binding sites) of EGFL7, and related transduction and transcription factors will be apparent to those of skill in the art.

Examples of molecular modeling systems are the CHARMm and QUANTA programs (Polygen Corporation, Waltham, Mass.). CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., *Acta Pharmaceutical Fennica* 97:159-166 (1988); Ripka, *New Scientist* 54-57 (Jun. 16, 1988); McKinaly and Rossmann, *Annu. Rev. Pharmacol. Toxiciol.* 29:111-122 (1989); Perry and Davies, OSAR: Quantitative Structure-Activity Relationships in Drug Design pp. 189-193 (Alan R. Liss, Inc. 1989); Lewis and Dean, *Proc. R. Soc. Lond.* 236:125-140 (1989) and 141-162; and, with respect to a model receptor for nucleic acid components, Askew, et al., *J. Am. Chem. Soc.* 111:1082-1090 (1989). Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Compounds identified via assays such as those described herein may be useful, for example, in elucidating the biological function of an EGFL7 gene product. Such compounds can be administered to a patient at therapeutically effective doses to treat any of a variety of physiological disorders. A therapeutically effective dose refers to that amount of the compound sufficient to result in any amelioration, impediment, prevention, or alteration of any biological symptom.

Assays for Compounds that Bind to EGFL7

Systems may be designed to identify compounds capable of interacting with (e.g., binding to) or mimicking EGFL7, or capable of interfering with the binding of EGFL7 to a cognate receptor, binding partner or substrate. The compounds identified can be useful, for example, in modulating the activity of wild type and/or mutant EGFL7 gene products; can be useful in elaborating the biological function of EGFL7; can be utilized in screens for identifying compounds that disrupt normal EGFL7 interactions; or may themselves disrupt or activate such interactions.

The principle of the assays used to identify compounds that bind to EGFL7, or EGFL7 cognate receptors or substrates, involves preparing a reaction mixture of EGFL7 and the test compound under conditions and for a time sufficient to allow the two components to interact and bind, thus forming a complex which can be removed and/or detected in the reaction mixture. The EGFL7 species used can vary depending upon the goal of the screening assay. For example, where agonists of the natural receptor are desired, the full-length EGFL7, or a soluble truncated EGFL7, a peptide, or fusion protein containing one or more EGFL7 domains fused to a protein or polypeptide that affords advantages in the assay system (e.g., labeling, isolation of the resulting complex, etc.) can be utilized. Where compounds that directly interact with EGFL7 are sought, peptides corresponding to the EGFL7 and fusion proteins containing EGFL7 can be used.

The screening assays can be conducted in a variety of ways. For example, one method to conduct such an assay would involve anchoring the EGFL7, polypeptide, peptide, or fusion protein therefrom, or the test substance onto a solid phase and detecting EGFL7/test compound complexes anchored on the solid phase at the end of the reaction. In one embodiment of such a method, the EGFL7 reactant may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for an EGFL7 protein, polypeptide, peptide or fusion protein or the test compound to anchor any complexes formed in solution, and a labeled antibody specific for the other component of the possible complex to detect anchored complexes.

Assays for Compounds that Interfere with EGFL7 Interactions

Macromolecules that interact with EGFL7 are referred to, for purposes of this discussion, as "binding partners". These binding partners are likely to be involved in EGFL7 mediated biological pathways. Therefore, it is desirable to identify compounds that interfere with or disrupt the interaction of such binding partners which may be useful in regulating or augmenting EGFL7 activity in the body and/or controlling disorders associated with this activity (or a deficiency thereof).

The basic principle of the assay systems used to identify compounds that interfere with the interaction between EGFL7 and a binding partner or partners involves preparing a reaction mixture containing EGFL7, or some variant thereof, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the EGFL7 and its binding partner. Control reaction mixtures are incubated without the test compound or with a placebo. The formation of any complexes between the EGFL7 and the binding partner is then detected. The formation of a complex in the control reaction, but not in the reaction mixture containing the test compound, indicates that the compound interferes with the interaction of the EGFL7 and the interactive binding partner. Additionally, complex formation within reaction mixtures containing the test compound and normal EGFL7 protein may also be compared to complex formation within reaction mixtures containing the test compound and a mutant EGFL7. This comparison may be important in those cases wherein it is desirable to identify compounds that specifically disrupt interactions of mutant, or mutated, EGFL7 but not the normal proteins.

The assay for compounds that interfere with the interaction between EGFL7 and binding partners can be conducted in a heterogeneous or homogeneous format. Heterogeneous assays involve anchoring either the EGFL7, or the binding partner, onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance; i.e., by adding the test substance to the reaction mixture prior to, or simultaneously with, EGFL7 and interactive binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either EGFL7 or an interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the EGFL7 or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of EGFL7 and an interactive binding partner is prepared in which either the EGFL7 or its binding partners is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances that disrupt the interaction can be identified.

In a particular embodiment, an EGFL7 fusion can be prepared for immobilization. For example, EGFL7, or a peptide fragment thereof, can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art and described above. This antibody can be labeled with the radioactive isotope $^{125}$I, for example, by methods routinely practiced in the art. In a heterogeneous assay, the fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between EGFL7 and the interactive binding partner can be detected by measuring the amount of radioactivity that remains associated with the glutathione-agarose beads. A successful inhibition of the interaction by the test compound will result in a decrease in measured radioactivity.

Alternatively, the GST fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the interaction between EGFL7 and the binding partner can be detected by adding the labeled antibody and measuring the radioactivity associated with the beads.

In another embodiment of the invention, these same techniques can be employed using peptide fragments that correspond to the binding domains of EGFL7 and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensatory mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a relatively short, labeled peptide comprising the binding domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

For example, and not by way of limitation, EGFL7 can be anchored to a solid material as described, above, by making a GST fusion protein and allowing it to bind to glutathione agarose beads. The interactive binding partner can be labeled with a radioactive isotope, such as $^{35}$S, and cleaved with a proteolytic enzyme such as trypsin. Cleavage products can then be added to the anchored fusion protein and allowed to bind. After washing away unbound peptides, labeled bound material, representing the intracellular binding partner binding domain, can be eluted, purified, and analyzed for amino acid sequence by well-known methods. Peptides so identified can be produced synthetically or fused to appropriate facilitative proteins using recombinant DNA technology.

Uses of EGFL7 Compositions
Assays for Cardiovascular, Endothelial, and Angiogenic Activity Various assays can be used to test the polypeptide herein for cardiovascular, endothelial, and angiogenic activity. Such assays include those provided in the Examples below.

Assays for tissue generation activity include, without limitation, those described in WO 95/16035 (bone, cartilage, tendon); WO 95/05846 (nerve, neuronal), and WO 91/07491 (skin, endothelium).

Assays for wound-healing activity include, for example, those described in Winter, *Epidermal Wound Healing*, Maibach, H I and Rovee, D T, eds. (Year Book Medical Publishers, Inc., Chicago), pp. 71-112, as modified by the article of Eaglstein and Mertz, *J. Invest. Dermatol.* 71:382-384 (1978).

There are several cardiac hypertrophy assays. In vitro assays include induction of spreading of adult rat cardiac myocytes. In this assay, ventricular myocytes are isolated from a single (male Sprague-Dawley) rat, essentially following a modification of the procedure described in detail by Piper et al., "Adult ventricular rat heart muscle cells" in *Cell*

Culture Techniques in Heart and Vessel Research, H. M. Piper, ed. (Berlin: Springer-Verlag, 1990), pp. 36-60. This procedure permits the isolation of adult ventricular myocytes and the long-term culture of these cells in the rod-shaped phenotype. Phenylephrine and Prostaglandin $F_{2\alpha}$ ($PGF_{2\alpha}$) have been shown to induce a spreading response in these adult cells. The inhibition of myocyte spreading induced by $PGF_{2\alpha}$ or $PGF_{2\alpha}$ analogs (e.g., fluprostenol) and phenylephrine by various potential inhibitors of cardiac hypertrophy is then tested.

For cancer, a variety of well-known animal models can be used to further understand the role of EGFL7 in the development and pathogenesis of tumors, and to test the efficacy of candidate therapeutic agents, including antibodies and other antagonists of native EGFL7 polypeptides, such as small-molecule antagonists. The in vivo nature of such models makes them particularly predictive of responses in human patients. Animal models of tumors and cancers (e.g., breast cancer, colon cancer, prostate cancer, lung cancer, etc.) include both non-recombinant and recombinant (transgenic) animals. Non-recombinant animal models include, for example, rodent, e.g., murine models. Such models can be generated by introducing tumor cells into syngeneic mice using standard techniques, e.g., subcutaneous injection, tail vein injection, spleen implantation, intraperitoneal implantation, implantation under the renal capsule, or orthopin implantation, e.g., colon cancer cells implanted in colonic tissue. See, e.g., PCT publication No. WO 97/33551, published Sep. 18, 1997. Probably the most often used animal species in oncological studies are immunodeficient mice and, in particular, nude mice. The observation that the nude mouse with thymic hypo/aplasia could successfully act as a host for human tumor xenografts has lead to its widespread use for this purpose. The autosomal recessive nu gene has been introduced into a very large number of distinct congenic strains of nude mouse, including, for example, ASW, A/He, AKR, BALB/c, B10.LP, C17, C3H, C57BL, C57, CBA, DBA, DDD, I/st, NC, NFR, NFS, NFS/N, NZB, NZC, NZW, P, RIII, and SJL. In addition, a wide variety of other animals with inherited immunological defects other than the nude mouse have been bred and used as recipients of tumor xenografts. For further details see, e.g., The Nude Mouse in Oncology Research, E. Boven and B. Winograd, eds. (CRC Press, Inc., 1991).

The cells introduced into such animals can be derived from known tumor/cancer cell lines, such as any of the above-listed tumor cell lines, and, for example, the B104-1-1 cell line (stable NIH-3T3 cell line transfected with the neu protooncogene); ras-transfected NIH-3T3 cells; Caco-2 (ATCC HTB-37); or a moderately well-differentiated grade II human colon adenocarcinoma cell line, HT-29 (ATCC HTB-38); or from tumors and cancers. Samples of tumor or cancer cells can be obtained from patients undergoing surgery, using standard conditions involving freezing and storing in liquid nitrogen. Karmali et al., Br. J. Cancer 48:689-696 (1983).

Tumor cells can be introduced into animals, such as nude mice or EGFL7 knockout mice, by a variety of procedures. The subcutaneous (s.c.) space in mice is very suitable for tumor implantation. Tumors can be transplanted s.c. as solid blocks, as needle biopsies by use of a trochar, or as cell suspensions. For solid-block or trochar implantation, tumor tissue fragments of suitable size are introduced into the s.c. space. Cell suspensions are freshly prepared from primary tumors or stable tumor cell lines, and injected subcutaneously. Tumor cells can also be injected as subdermal implants. In this location, the inoculum is deposited between the lower part of the dermal connective tissue and the s.c. tissue.

Animal models of breast cancer can be generated, for example, by implanting rat neuroblastoma cells (from which the neu oncogene was initially isolated), or neu-transformed NIH-3T3 cells into nude mice, essentially as described by Drebin et al. Proc. Nat. Acad. Sci. USA 83:9129-9133 (1986).

Similarly, animal models of colon cancer can be generated by passaging colon cancer cells in animals, e.g., nude mice, leading to the appearance of tumors in these animals. An orthotopic transplant model of human colon cancer in nude mice has been described, for example, by Wang et al., Cancer Research 54:4726-4728 (1994) and Too et al., Cancer Research 55:681-684 (1995). This model is based on the so-called "METAMOUSE™" sold by AntiCancer, Inc., (San Diego, Calif.).

Tumors that arise in animals can be removed and cultured in vitro. Cells from the in vitro cultures can then be passaged to animals. Such tumors can serve as targets for further testing or drug screening. Alternatively, the tumors resulting from the passage can be isolated and RNA from pre-passage cells and cells isolated after one or more rounds of passage analyzed for differential expression of genes of interest. Such passaging techniques can be performed with any known tumor or cancer cell lines.

For example, Meth A, CMS4, CMS5, CMS21, and WEHI-164 are chemically induced fibrosarcomas of BALB/c female mice (DeLeo et al., J. Exp. Med. 146:720 (1977)), which provide a highly controllable model system for studying the anti-tumor activities of various agents. Palladino et al., J. Immunol. 138:4023-4032 (1987). Briefly, tumor cells are propagated in vitro in cell culture. Prior to injection into the animals, the cell lines are washed and suspended in buffer, at a cell density of about $10 \times 10^6$ to $10 \times 10^7$ cells/ml. The animals are then infected subcutaneously with 10 to 100 µl of the cell suspension, allowing one to three weeks for a tumor to appear.

In addition, the Lewis lung carcinoma of mice, which is one of the most thoroughly studied experimental tumors, can be used as an investigational tumor model. Efficacy in this tumor model has been correlated with beneficial effects in the treatment of human patients diagnosed with small-cell carcinoma of the lung (SCCL). This tumor can be introduced in normal mice upon injection of tumor fragments from an affected mouse or of cells maintained in culture. Zupi et al., Br. J. Cancer 41:suppl. 4, 30 (1980). Evidence indicates that tumors can be started from injection of even a single cell and that a very high proportion of infected tumor cells survive. For further information about this tumor model see, Zacharski, Haemostasis 16:300-320 (1986).

One way of evaluating the efficacy of a test compound in an animal model with an implanted tumor is to measure the size of the tumor before and after treatment. Traditionally, the size of implanted tumors has been measured with a slide caliper in two or three dimensions. The measure limited to two dimensions does not accurately reflect the size of the tumor; therefore, it is usually converted into the corresponding volume by using a mathematical formula. However, the measurement of tumor size is very inaccurate. The therapeutic effects of a drug candidate can be better described as treatment-induced growth delay and specific growth delay. Another important variable in the description of tumor growth is the tumor volume doubling time. Computer programs for the calculation and description of tumor growth are also available, such as the program reported by Rygaard and Spang-Thomsen, Proc. 6th Int. Workshop on Immune-Deficient Animals, Wu and Sheng eds. (Basel, 1989), p. 301. It is noted, however, that necrosis and inflammatory responses following treatment may actually result in an increase in tumor size, at least initially.

Therefore, these changes need to be carefully monitored, by a combination of a morphometric method and flow cytometric analysis.

Further, recombinant (transgenic) animal models can be engineered by introducing the coding portion of the EGFL7 gene identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g., baboons, chimpanzees and monkeys. Techniques known in the art to introduce a transgene into such animals include pronucleic microinjection (U.S. Pat. No. 4,873,191); retrovirus-mediated gene transfer into germ lines (e.g., Van der Putten et al., Proc. Natl. Acad. Sci. USA 82:6148-615 (1985)); gene targeting in embryonic stem cells (Thompson et al., Cell 56:313-321 (1989)); electroporation of embryos (Lo, Mol. Cell. Biol. 3:1803-1814 (1983)); and sperm-mediated gene transfer. Lavitrano et al., Cell 57:717-73 (1989). For a review, see for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., Proc. Natl. Acad. Sci. USA 89:6232-636 (1992). The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry. The animals are further examined for signs of tumor or cancer development.

Alternatively, "knock-out" animals can be constructed that have a defective or altered gene encoding EGFL7 identified herein, as a result of homologous recombination between the endogenous gene encoding EGFL7 and altered genomic DNA encoding the same polypeptide introduced into an embryonic cell of the animal. For example, cDNA encoding a particular EGFL7 polypeptide can be used to clone genomic DNA encoding that polypeptide in accordance with established techniques. A portion of the genomic DNA encoding a particular EGFL7 polypeptide can be deleted or replaced with another gene, such as a gene encoding a selectable marker that can be used to monitor integration. Typically, several kilobases of unaltered flanking DNA (both at the 5' and 3' ends) are included in the vector. See, e.g., Thomas and Capecchi, Cell 51:503 (1987) for a description of homologous recombination vectors. The vector is introduced into an embryonic stem cell line (e.g., by electroporation) and cells in which the introduced DNA has homologously recombined with the endogenous DNA are selected. See, e.g., Li et al., Cell 69:915 (1992). The selected cells are then injected into a blastocyst of an animal (e.g., a mouse or rat) to form aggregation chimeras. See, e.g., Bradley, in Teratocarcinomas and Embryonic Stem Cells: A Practical Approach, E. J. Robertson, ed. (IRL: Oxford, 1987), pp. 113-152. A chimeric embryo can then be implanted into a suitable pseudopregnant female foster animal and the embryo brought to term to create a "knock-out" animal. Progeny harboring the homologously recombined DNA in their germ cells can be identified by standard techniques and used to breed animals in which all cells of the animal contain the homologously recombined DNA. Knockout animals can be characterized, for instance, by their ability to defend against certain pathological conditions and by their development of pathological conditions due to absence of EGFL7.

The efficacy of antibodies specifically binding EGFL7 identified herein, and other drug candidates, can be tested also in the treatment of spontaneous animal tumors. A suitable target for such studies is the feline oral squamous cell carcinoma (SCC). Feline oral SCC is a highly invasive, malignant tumor that is the most common oral malignancy of cats, accounting for over 60% of the oral tumors reported in this species. It rarely metastasizes to distant sites, although this low incidence of metastasis may merely be a reflection of the short survival times for cats with this tumor. These tumors are usually not amenable to surgery, primarily because of the anatomy of the feline oral cavity. At present, there is no effective treatment for this tumor. Prior to entry into the study, each cat undergoes complete clinical examination and biopsy, and is scanned by computed tomography (CT). Cats diagnosed with sublingual oral squamous cell tumors are excluded from the study. The tongue can become paralyzed as a result of such tumor, and even if the treatment kills the tumor, the animals may not be able to feed themselves. Each cat is treated repeatedly, over a longer period of time. Photographs of the tumors will be taken daily during the treatment period, and at each subsequent recheck. After treatment, each cat undergoes another CT scan. CT scans and thoracic radiograms are evaluated every 8 weeks thereafter. The data are evaluated for differences in survival, response, and toxicity as compared to control groups. Positive response may require evidence of tumor regression, preferably with improvement of quality of life and/or increased life span.

In addition, other spontaneous animal tumors, such as fibrosarcoma, adenocarcinoma, lymphoma, chondroma, or leiomyosarcoma of dogs, cats, and baboons can also be tested. Of these, mammary adenocarcinoma in dogs and cats is a preferred model as its appearance and behavior are very similar to those in humans. However, the use of this model is limited by the rare occurrence of this type of tumor in animals.

Other in vitro and in vivo cardiovascular, endothelial, and angiogenic tests known in the art are also suitable herein.

Tissue Distribution

The results of the cardiovascular, endothelial, and angiogenic assays herein can be verified by further studies, such as by determining mRNA expression in various human tissues.

As noted before, gene amplification and/or gene expression in various tissues may be measured by conventional Southern blotting, Northern blotting to quantitate the transcription of mRNA (Thomas, Proc. Natl. Acad. Sci. USA 77:5201-5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes.

Gene expression in various tissues, alternatively, may be measured by immunological methods, such as immunohistochemical staining of tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native-sequence EGFL7 polypeptide or against a synthetic peptide based on the DNA sequences provided herein or against exogenous sequence fused to EGFL7 DNA and encoding a specific antibody epitope. General techniques for generating antibodies, and special protocols for in situ hybridization are provided herein below.

Antibody Binding Studies

The results of the cardiovascular, endothelial, and angiogenic study can be further verified by antibody binding studies, in which the ability of anti-EGFL7 antibodies to inhibit the effect of EGFL7s on endothelial cells or other cells used in the cardiovascular, endothelial, and angiogenic assays is tested. Exemplary antibodies include polyclonal, monoclonal, humanized, bispecific, and heteroconjugate antibodies, the preparation of which will be described hereinbelow.

Antibody binding studies may be carried out in any known assay method, such as competitive binding assays, direct and indirect sandwich assays, and immunoprecipitation assays. Zola, *Monoclonal Antibodies: A Manual of Techniques* (CRC Press, Inc., 1987), pp. 147-158.

Competitive binding assays rely on the ability of a labeled standard to compete with the test sample analyte for binding with a limited amount of antibody. The amount of target protein in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte that remain unbound.

Sandwich assays involve the use of two antibodies, each capable of binding to a different immunogenic portion, or epitope, of the protein to be detected. In a sandwich assay, the test sample analyte is bound by a first antibody that is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tissue sample may be fresh or frozen or may be embedded in paraffin and fixed with a preservative such as formalin, for example.

Cell-Based Tumor Assays

Cell-based assays and animal models for cardiovascular, endothelial, and angiogenic disorders, such as tumors, can be used to verify the findings of a cardiovascular, endothelial, and angiogenic assay herein, and further to understand the relationship between the gene identified herein and the development and pathogenesis of undesirable cardiovascular, endothelial, and angiogenic cell growth. The role of gene products identified herein in the development and pathology of undesirable cardiovascular, endothelial, and angiogenic cell growth, e.g., tumor cells, can be tested by using cells or cells lines that have been identified as being stimulated or inhibited by EGFL7 herein. Such cells include, for example, those set forth in the Examples below.

In a different approach, cells of a cell type known to be involved in a particular cardiovascular, endothelial, and angiogenic disorder are transfected with the cDNAs herein, and the ability of these cDNAs to induce excessive growth or inhibit growth is analyzed. If the cardiovascular, endothelial, and angiogenic disorder is cancer, suitable tumor cells include, for example, stable tumor cell lines such as the B104-1-1 cell line (stable NIH-3T3 cell line transfected with the neu protooncogene) and ras-transfected NIH-3T3 cells, which can be transfected with the desired gene and monitored for tumorigenic growth. Such transfected cell lines can then be used to test the ability of poly- or monoclonal antibodies or antibody compositions to inhibit tumorigenic cell growth by exerting cytostatic or cytotoxic activity on the growth of the transformed cells, or by mediating antibody-dependent cellular cytotoxicity (ADCC). Cells transfected with the coding sequences of the gene identified herein can further be used to identify drug candidates for the treatment of cardiovascular, endothelial, and angiogenic disorders such as cancer.

In addition, primary cultures derived from tumors in transgenic animals (as described above) can be used in the cell-based assays herein, although stable cell lines are preferred. Techniques to derive continuous cell lines from transgenic animals are well known in the art. See, e.g., Small et al., *Mol. Cell. Biol.* 5:642-648 (1985).

Use of Gene as a Diagnostic

This invention is also related to the use of the gene encoding EGFL7 as a diagnostic. Detection of a mutated form of EGFL7 will allow a diagnosis of a cardiovascular, endothelial, and angiogenic disease or a susceptibility to a cardiovascular, endothelial, and angiogenic disease, such as a tumor.

Individuals carrying mutations in the gene encoding a human EGFL7 polypeptide may be detected at the DNA level by a variety of techniques. Nucleic acids for diagnosis may be obtained from a patient's cells, such as from blood, urine, saliva, tissue biopsy, and autopsy material. The genomic DNA may be used directly for detection or may be amplified enzymatically by using PCR (Saiki et al., *Nature* 324:163-166 (1986)) prior to analysis. RNA or cDNA may also be used for the same purpose. As an example, PCR primers complementary to the nucleic acid encoding EGFL7 can be used to identify and analyze EGFL7 mutations. For example, deletions and insertions can be detected by a change in size of the amplified product in comparison to the normal genotype. Point mutations can be identified by hybridizing amplified DNA to radiolabeled RNA encoding EGFL7, or alternatively, radiolabeled antisense DNA sequences encoding EGFL7. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamidine gradient gels in which the mobilities of different DNA fragments are retarded in the gel at different positions according to their specific melting or partial melting temperatures. See, e.g., Myers et al., *Science* 230:1242 (1985).

Sequence changes at specific locations may also be revealed by nuclease protection assays, such as RNase and S1 protection or the chemical cleavage method, for example, Cotton et al., *Proc. Natl. Acad. Sci. USA* 85:4397-4401 (1985).

Thus, the detection of a specific DNA sequence may be achieved by methods such as hybridization, RNase protection, chemical cleavage, direct DNA sequencing, or the use of restriction enzymes, e.g., restriction fragment length polymorphisms (RFLP), and Southern blotting of genomic DNA.

Use to Detect Polypeptide Expression Levels

In addition to more conventional gel-electrophoresis and DNA sequencing, mutations can also be detected by in situ analysis.

Expression of nucleic acid encoding EGFL7 may be linked to vascular disease or neovascularization associated with tumor formation. If EGFL7 has a signal sequence and the mRNA is highly expressed in endothelial cells and to a lesser extent in smooth muscle cells, this indicates that EGFL7 is present in serum. Accordingly, an anti-EGFL7 polypeptide antibody could be used to diagnose vascular disease or neovascularization associated with tumor formation, since an altered level of this EGFL7 polypeptide may be indicative of such disorders.

A competition assay may be employed wherein antibodies specific to EGFL7 are attached to a solid support and the labeled EGFL7 polypeptide and a sample derived from the host are passed over the solid support and the amount of label detected attached to the solid support can be correlated to a quantity of EGFL7 in the sample.

Chromosome Mapping

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15-25 bp) from the cDNA. Computer analysis for the 3'-untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes, and preselection by hybridization to construct chromosome-specific cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the gene encoding EGFL7 was derived, and the longer the better. For example, 2,000 bp is good, 4,000 bp is better, and more than 4,000 is probably not necessary to get good results a reasonable percentage of the time. For a review of this technique, see, Verma et al., *Human Chromosomes: a Manual of Basic Techniques* (Pergamon Press, New York, 1988).

Once a sequence has been mapped to a precise chromosomal location, the physical position of the sequence on the chromosome can be correlated with genetic map data. Such data are found, for example, in V. McKusick, *Mendelian Inheritance in Man* (available online through Johns Hopkins University Welch Medical Library). The relationship between genes and diseases that have been mapped to the same chromosomal region is then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Screening Assays for Drug Candidates

This invention encompasses methods of screening compounds to identify those that mimic EGFL7 (agonists) or prevent the effect of EGFL7 (antagonists). Screening assays for antagonist drug candidates are designed to identify compounds that bind or complex with EGFL7, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with EGFL7 under conditions and for a time sufficient to allow these two components to interact.

In binding assays, the interaction is binding and the complex formed can be isolated or detected in the reaction mixture. In a particular embodiment, EGFL7 or the drug candidate is immobilized on a solid phase, e.g., on a microtiter plate, by covalent or non-covalent attachments. Non-covalent attachment generally is accomplished by coating the solid surface with a solution of EGFL7 and drying. Alternatively, an immobilized antibody, e.g., a monoclonal antibody, specific for EGFL7 to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular EGFL7 polypeptide, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)* 340:245-246 (1989); Chien et al., *Proc. Natl. Acad. Sci. USA* 88:9578-9582 (1991)) as disclosed by Chevray and Nathans, *Proc. Natl. Acad. Sci. USA* 89:5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of EGFL7 and other intra- or extracellular components can be tested as follows: usually a reaction mixture is prepared containing EGFL7 and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

EGFL7 antagonists may be detected by combining EGFL7 and a potential antagonist with membrane-bound EGFL7 polypeptide receptors or recombinant receptors under appropriate conditions for a competitive inhibition assay. EGFL7 can be labeled, such as by radioactivity, such that the number of EGFL7 polypeptide molecules bound to the receptor can be used to determine the effectiveness of the potential antagonist. The gene encoding the receptor can be identified by numerous methods known to those of skill in the art, for example, ligand panning and FACS sorting. Coligan et al., Current Protocols in Immun. 1(2):Chapter 5 (1991). Preferably, expression cloning is employed wherein polyadenylated RNA is prepared from a cell responsive to EGFL7 and a cDNA library created from this RNA is divided into pools and used to transfect COS cells or other cells that are not responsive to EGFL7. Transfected cells that are grown on glass slides are exposed to the labeled EGFL7 polypeptide. EGFL7 can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, the labeled EGFL7 polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with the labeled EGFL7 polypeptide in the presence of the candidate compound. The ability of the compound to enhance or block this interaction could then be measured.

The compositions useful in the treatment of cardiovascular, endothelial, and angiogenic disorders include, without limitation, antibodies, small organic and inorganic molecules, peptides, phosphopeptides, antisense and ribozyme molecules, triple-helix molecules, etc., that inhibit the expression and/or activity of the target gene product.

More specific examples of potential antagonists include an oligonucleotide that binds to the fusions of immunoglobulin with EGFL7, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of EGFL7 that recognizes the receptor but imparts no effect, thereby competitively inhibiting the action of EGFL7.

Another potential EGFL7 antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature EGFL7 polypeptides herein, is used to design an antisense RNA oligonucleotide of from about 10 to 40 base pairs in length. A DNA oligonucleotide is designed to be complementary to a region of the gene involved in transcription (triple helix—see, Lee et al., Nucl. Acids Res. 6:3073 (1979); Cooney et al., Science 241:456 (1988); Dervan et al., Science 251:1360 (1991)), thereby preventing transcription and the production of EGFL7. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex helix formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex. The antisense RNA oligonucleotide hybridizes to the mRNA in vivo and blocks translation of the mRNA molecule into EGFL7 (antisense—Okano, Neurochem. 56:560 (1991); Oligodeoxynucleotides as Antisense Inhibitors of Gene Expression (CRC Press: Boca Raton, Fla., 1988).

The antisense oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., *Proc. Natl. Acad. Sci. U.S.A.* 86:6553-6556 (1989); Lemaitre, et al., *Proc. Natl. Acad. Sci. U.S.A.* 84:648-652 (1987); PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., *BioTechniques* 6:958-976 (1988)) or intercalating agents (see, e.g., Zon, *Pharm. Res.* 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an -anomeric oligonucleotide. An -anomeric oligonucleotide forms specific double-stranded hybrids with complementary RNA in which, contrary to the usual—units, the strands run parallel to each other (Gautier, et al., *Nucl. Acids Res.* 15:6625-6641 (1987)). The oligonucleotide is a 2'-O-methylribonucleotide (Inoue, et al., *Nucl. Acids Res.* 15:6131-6148 (1987)), or a chimeric RNA-DNA analogue (Inoue, et al., *FEBS Lett.* 215:327-330 (1987)).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein, et al. (*Nucl. Acids Res.* 16:3209 (1988)), methylphosphonate oligonucleotides can be prepared by use of controlled pore glass polymer supports (Sarin, et al., *Proc. Natl. Acad. Sci. U.S.A.* 85:7448-7451 (1988)), etc.

The oligonucleotides described above can also be delivered to cells such that the antisense RNA or DNA may be expressed in vivo to inhibit production of EGFL7. When antisense DNA is used, oligodeoxyribonucleotides derived from the translation-initiation site, e.g., between about −10 and +10 positions of the target gene nucleotide sequence, are preferred.

Antisense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

Potential antagonists further include small molecules that bind to the active site, the receptor binding site, or growth factor or other relevant binding site of EGFL7, thereby blocking the normal biological activity of EGFL7. Examples of small molecules include, but are not limited to, small peptides or peptide-like molecules, preferably soluble peptides, and synthetic non-peptidyl organic or inorganic compounds.

Additional potential antagonists are ribozymes, which are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology* 4:469-471 (1994), and PCT publication No. WO 97/33551 (published Sep. 18, 1997).

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions which form complementary base pairs with the target mRNA. The sole requirement is that the target mRNA have the following sequence of two bases: 5'-UG-3'. The construction and production of hammerhead ribozymes is well known in the art and is described more fully in Myers, *Molecular Biology and Biotechnology: A Comprehensive Desk Reference*, VCH Publishers, New York (1995), (see especially FIG. 4, page 833) and in Haseloff and Gerlach, *Nature,* 334:585-591 (1988), which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., *Science,* 224:574-578 (1984); Zaug and Cech, *Science,* 231:470-475 (1986); Zaug, et al., *Nature,* 324:429-433 (1986); published International patent application No. WO 88/04300 by University Patents Inc.; Been and Cech, *Cell,* 47:207-216 (1986)). The Cech-type ribozymes have an eight base pair active site that hybridizes to a target RNA sequence whereafter cleavage of the target RNA takes place. The invention encompasses those Cech-type ribozymes that target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes, unlike antisense molecules, are catalytic, a lower intracellular concentration is required for efficiency.

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Types of Cardiovascular, Endothelial, and Angiogenic Disorders to be Treated

EGFL7 or agonists thereto that have activity in the cardiovascular, angiogenic, and endothelial assays described herein, are likely to have therapeutic uses in a variety of cardiovascular, endothelial, and angiogenic disorders, including systemic disorders that affect vessels, such as diabetes mellitus. Their therapeutic utility could include diseases of the arteries, capillaries, veins, and/or lymphatics. Examples of treatments hereunder include treating muscle wasting disease, treating osteoporosis, aiding in implant fixation to stimulate the growth of cells around the implant and therefore facilitate its attachment to its intended site, increasing IGF stability in tissues or in serum, if applicable, and increasing binding to the IGF receptor (since IGF has been shown in vitro to enhance human marrow erythroid and granulocytic progenitor cell growth).

EGFL7 or agonists thereto may also be employed to stimulate erythropoiesis or granulopoiesis, to stimulate wound healing or tissue regeneration and associated therapies concerned with re-growth of tissue, such as connective tissue, skin, bone, cartilage, muscle, lung, or kidney, to promote angiogenesis, to stimulate or inhibit migration of endothelial cells, and to proliferate the growth of vascular smooth muscle and endothelial cell production. The increase in angiogenesis mediated by EGFL7 or agonist would be beneficial to ischemic tissues and to collateral coronary development in the heart subsequent to coronary stenosis. Antagonists are used to inhibit the action of such polypeptides, for example, to limit the production of excess connective tissue during wound healing or pulmonary fibrosis if EGFL7 promotes such production. This would include treatment of acute myocardial infarction and heart failure.

Specific types of diseases are described below, where EGFL7 may serve as useful for vascular-related drug targeting or as therapeutic targets for the treatment or prevention of the disorders. Atherosclerosis is a disease characterized by accumulation of plaques of intimal thickening in arteries, due to accumulation of lipids, proliferation of smooth muscle cells, and formation of fibrous tissue within the arterial wall. The disease can affect large, medium, and small arteries in any organ. Changes in endothelial and vascular smooth muscle cell function are known to play an important role in modulating the accumulation and regression of these plaques.

Hypertension is characterized by raised vascular pressure in the systemic arterial, pulmonary arterial, or portal venous systems. Elevated pressure may result from or result in impaired endothelial function and/or vascular disease.

Inflammatory vasculitides include giant cell arteritis, Takayasu's arteritis, polyarteritis nodosa (including the microangiopathic form), Kawasaki's disease, microscopic polyangiitis, Wegener's granulomatosis, and a variety of infectious-related vascular disorders (including Henoch-Schonlein prupura). Altered endothelial cell function has been shown to be important in these diseases.

Reynaud's disease and Reynaud's phenomenon are characterized by intermittent abnormal impairment of the circulation through the extremities on exposure to cold. Altered endothelial cell function has been shown to be important in this disease.

Aneurysms are saccular or fusiform dilatations of the arterial or venous tree that are associated with altered endothelial cell and/or vascular smooth muscle cells.

Arterial restenosis (restenosis of the arterial wall) may occur following angioplasty as a result of alteration in the function and proliferation of endothelial and vascular smooth muscle cells.

Thrombophlebitis and lymphangitis are inflammatory disorders of veins and lymphatics, respectively, that may result from, and/or in, altered endothelial cell function. Similarly, lymphedema is a condition involving impaired lymphatic vessels resulting from endothelial cell function.

The family of benign and malignant vascular tumors are characterized by abnormal proliferation and growth of cellular elements of the vascular system. For example, lymphangiomas are benign tumors of the lymphatic system that are congenital, often cystic, malformations of the lymphatics that usually occur in newborns. Cystic tumors tend to grow into the adjacent tissue. Cystic tumors usually occur in the cervical and axillary region. They can also occur in the soft tissue of the extremities. The main symptoms are dilated, sometimes reticular, structured lymphatics and lymphocysts surrounded by connective tissue. Lymphangiomas are assumed to be caused by improperly connected embryonic lymphatics or their deficiency. The result is impaired local lymph drainage. Griener et al., *Lymphology* 4:140-144 (1971).

Another use for EGFL7 antagonists is in the prevention of tumor angiogenesis, which involves vascularization of a tumor to enable it to growth and/or metastasize. This process is dependent on the growth of new blood vessels. Examples of neoplasms and related conditions that involve tumor angiogenesis include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

The EGFL7 antagonists can also be useful in treating intraocular neovascular diseases including, but not limited to, proliferative retinopathies, choroidal neovascularization (CNV), age-related macular degeneration (AMD), diabetic and other ischemia-related retinopathies, diabetic macular edema, pathological myopia, von Hippel-Lindau disease, histoplasmosis of the eye, Central Retinal Vein Occlusion (CRVO), corneal neovascularization, retinal neovascularization, etc.

Rheumatoid arthritis is a further indication. Blood vessel growth and targeting of inflammatory cells through the vasculature is an important component in the pathogenesis of rheumatoid and sero-negative forms of arthritis.

In view of the above, EGFL7, agonists or antagonists thereof described herein, which are shown to alter or impact endothelial cell function and migration, are likely to play an important role in the etiology and pathogenesis of many or all of the disorders noted above, and as such can serve as therapeutic targets to augment or inhibit these processes or for vascular-related drug targeting in these disorders.

Administration Protocols, Schedules, Doses, and Formulations

The molecules herein and agonists and antagonists thereto are pharmaceutically useful as a prophylactic and therapeutic agent for various disorders and diseases as set forth above.

Therapeutic compositions of EGFL7s or agonists or antagonists are prepared for storage by mixing the desired molecule having the appropriate degree of purity with optional pharmaceutically acceptable carriers, excipients, or stabilizers (Remington's Pharmaceutical Sciences, 16th edition, Osol, A. ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Additional examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of agonist or antagonist include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations. EGFL7s or agonists or antagonists will typically be formulated in such vehicles at a concentration of about 0.1 mg/ml to 100 mg/ml.

Another formulation comprises incorporating EGFL7 or agonist or antagonist thereof into formed articles. Such articles can be used in modulating endothelial cell growth and angiogenesis. In addition, tumor invasion and metastasis may be modulated with these articles.

EGFL7 polypeptides or agonists or antagonists to be used for in vivo administration must be sterile. This is readily accomplished by filtration through sterile filtration membranes, prior to or following lyophilization and reconstitution. EGFL7 polypeptides ordinarily will be stored in lyophilized form or in solution if administered systemically. If in lyophilized form, EGFL7 or agonist or antagonist thereto is typically formulated in combination with other ingredients for reconstitution with an appropriate diluent at the time for use. An example of a liquid formulation of EGFL7 or agonist or antagonist is a sterile, clear, colorless unpreserved solution filled in a single-dose vial for subcutaneous injection. Preserved pharmaceutical compositions suitable for repeated use may contain, for example, depending mainly on the indication and type of polypeptide:

EGFL7 polypeptide or agonist or antagonist thereto;

a buffer capable of maintaining the pH in a range of maximum stability of the polypeptide or other molecule in solution, preferably about 4-8;

a detergent/surfactant primarily to stabilize the polypeptide or molecule against agitation-induced aggregation;

an isotonifier;

a preservative selected from the group of phenol, benzyl alcohol and a benzethonium halide, e.g., chloride; and water.

If the detergent employed is non-ionic, it may, for example, be polysorbates (e.g., POLYSORBATE™ (TWEEN™) 20, 80, etc.) or poloxamers (e.g., POLOXAMER™ 188). The use of non-ionic surfactants permits the formulation to be exposed to shear surface stresses without causing denaturation of the polypeptide. Further, such surfactant-containing formulations may be employed in aerosol devices such as those used in a pulmonary dosing, and needleless jet injector guns (see, e.g., EP 257,956).

An isotonifier may be present to ensure isotonicity of a liquid composition of EGFL7 or agonist or antagonist thereto, and includes polyhydric sugar alcohols, preferably trihydric or higher sugar alcohols, such as glycerin, erythritol, arabitol, xylitol, sorbitol, and mannitol. These sugar alcohols can be used alone or in combination. Alternatively, sodium chloride or other appropriate inorganic salts may be used to render the solutions isotonic.

The buffer may, for example, be an acetate, citrate, succinate, or phosphate buffer depending on the pH desired. The pH of one type of liquid formulation of this invention is buffered in the range of about 4 to 8, preferably about physiological pH.

The preservatives phenol, benzyl alcohol and benzethonium halides, e.g., chloride, are known antimicrobial agents that may be employed.

Therapeutic polypeptide compositions described herein generally are placed into a container having a sterile access port, for example, an intravenous solution bag or vial having a stopper pierceable by a hypodermic injection needle. The formulations are preferably administered as repeated intravenous (i.v.), subcutaneous (s.c.), or intramuscular (i.m.) injections, or as aerosol formulations suitable for intranasal or intrapulmonary delivery (for intrapulmonary delivery see, e.g., EP 257,956).

Therapeutic polypeptides can also be administered in the form of sustained-released preparations. Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.* 15:167-277 (1981) and Langer, *Chem. Tech.* 12:98-105 (1982) or poly(vinylalcohol)), polylactides (U.S. Pat. No. 3,773,919, EP 58,481), copolymers of L-glutamic acid and gamma ethyl-L-glutamate (Sidman et al., *Biopolymers* 22:547-556 (1983)), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37 C, resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release EGFL7 polypeptide compositions also include liposomally entrapped EGFL7 polypeptides. Liposomes containing the EGFL7 polypeptide are prepared by methods known per se: DE 3,218,121; Epstein et al., *Proc. Natl. Acad. Sci. USA* 82:3688-3692 (1985); Hwang et al., *Proc. Natl. Acad. Sci. USA* 77:4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamellar type in which the lipid content is greater than about 30 mol. % cholesterol, the selected proportion being adjusted for the optimal therapy.

The therapeutically effective dose of EGFL7 or agonist or antagonist thereto will, of course, vary depending on such factors as the pathological condition to be treated (including prevention), the method of administration, the type of compound being used for treatment, any co-therapy involved, the patient's age, weight, general medical condition, medical history, etc., and its determination is well within the skill of a practicing physician. Accordingly, it will be necessary for the therapist to titer the dosage and modify the route of administration as required to obtain the maximal therapeutic effect. If EGFL7 has a narrow host range, for the treatment of human patients formulations comprising human EGFL7 polypeptide, more preferably native-sequence human EGFL7 polypeptide, are preferred. The clinician will administer EGFL7 until a dosage is reached that achieves the desired effect for treatment of the condition in question. For example, if the objective is the treatment of CHF, the amount would be one that inhibits the progressive cardiac hypertrophy associated with this condition. The progress of this therapy is easily monitored by echo cardiography. Similarly, in patients with hypertrophic cardiomyopathy, EGFL7 can be administered on an empirical basis.

With the above guidelines, the effective dose generally is within the range of from about 0.001 to about 1.0 mg/kg, more preferably about 0.01-1.0 mg/kg, most preferably about 0.01-0.1 mg/kg.

For non-oral use in treating human adult hypertension, it is advantageous to administer EGFL7 in the form of an injection at about 0.01 to 50 mg, preferably about 0.05 to 20 mg, most preferably 1 to 20 mg, per kg body weight, 1 to 3 times daily by intravenous injection. For oral administration, a molecule based on EGFL7 is preferably administered at about 5 mg to 1 g, preferably about 10 to 100 mg, per kg body weight, 1 to 3 times daily. It should be appreciated that endotoxin contamination should be kept minimally at a safe level, for example, less than 0.5 ng/mg protein. Moreover, for human administration, the formulations preferably meet sterility, pyrogenicity, general safety, and purity as required by FDA Office and Biologics standards.

The dosage regimen of a pharmaceutical composition containing EGFL7 to be used in tissue regeneration will be determined by the attending physician considering various factors that modify the action of the polypeptides, e.g., amount of tissue weight desired to be formed, the site of damage, the condition of the damaged tissue, the size of a wound, type of damaged tissue (e.g., bone), the patient's age, sex, and diet, the severity of any infection, time of administration, and other clinical factors. The dosage may vary with the type of matrix used in the reconstitution and with inclusion of other proteins in the pharmaceutical composition. For example, the addition of other known growth factors, such as IGF-I, to the final composition may also affect the dosage. Progress can be monitored by periodic assessment of tissue/bone growth and/or repair, for example, X-rays, histomorphometric determinations, and tetracycline labeling.

The route of EGFL7 polypeptide or antagonist or agonist administration is in accord with known methods, e.g., by injection or infusion by intravenous, intramuscular, intracerebral, intraperitoneal, intracerobrospinal, subcutaneous, intraocular, intraarticular, intrasynovial, intrathecal, oral, topical, or inhalation routes, or by sustained-release systems as noted below. EGFL7 or agonist or antagonists thereof also are suitably administered by intratumoral, peritumoral, intralesional, or perilesional routes, to exert local as well as systemic therapeutic effects. The intraperitoneal route is expected to be particularly useful, for example, in the treatment of ovarian tumors.

If a peptide or small molecule is employed as an antagonist or agonist, it is preferably administered orally or non-orally in the form of a liquid or solid to mammals.

Examples of pharmacologically acceptable salts of molecules that form salts and are useful hereunder include alkali metal salts (e.g., sodium salt, potassium salt), alkaline earth metal salts (e.g., calcium salt, magnesium salt), ammonium salts, organic base salts (e.g., pyridine salt, triethylamine salt), inorganic acid salts (e.g., hydrochloride, sulfate, nitrate), and salts of organic acid (e.g., acetate, oxalate, p-toluenesulfonate).

For compositions herein that are useful for bone, cartilage, tendon, or ligament regeneration, the therapeutic method includes administering the composition topically, systemically, or locally as an implant or device. When administered, the therapeutic composition for use is in a pyrogen-free, physiologically acceptable form. Further, the composition may desirably be encapsulated or injected in a viscous form for delivery to the site of bone, cartilage, or tissue damage. Topical administration may be suitable for wound healing and tissue repair. Preferably, for bone and/or cartilage formation, the composition would include a matrix capable of delivering the protein-containing composition to the site of bone and/or cartilage damage, providing a structure for the developing bone and cartilage and preferably capable of being resorbed into the body. Such matrices may be formed of materials presently in use for other implanted medical applications.

The choice of matrix material is based on biocompatibility, biodegradability, mechanical properties, cosmetic appearance, and interface properties. The particular application of the compositions will define the appropriate formulation. Potential matrices for the compositions may be biodegradable and chemically defined calcium sulfate, tricalcium phosphate, hydroxyapatite, polylactic acid, polyglycolic acid, and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above-mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

One specific embodiment is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the polypeptide compositions from disassociating from the matrix.

One suitable family of sequestering agents is cellulosic materials such as alkylcelluloses (including hydroxyalkylcelluloses), including methylcellulose, ethylcellulose, hydroxyethylcellulose, hydroxypropylcellulose, hydroxypropylmethylcellulose, and carboxymethylcellulose, one preferred being cationic salts of carboxymethylcellulose (CMC). Other preferred sequestering agents include hyaluronic acid, sodium alginate, poly(ethylene glycol), polyoxyethylene oxide, carboxyvinyl polymer, and poly(vinyl alcohol). The amount of sequestering agent useful herein is 0.5-20 wt %, preferably 1-10 wt %, based on total formulation weight, which represents the amount necessary to prevent desorption of the polypeptide (or its antagonist) from the polymer matrix and to provide appropriate handling of the composition, yet not so much that the progenitor cells are prevented from infiltrating the matrix, thereby providing the polypeptide (or its antagonist) the opportunity to assist the osteogenic activity of the progenitor cells.

Combination Therapies

The effectiveness of EGFL7 or an agonist or antagonist thereof in preventing or treating the disorder in question may be improved by administering the active agent serially or in combination with another agent that is effective for those purposes, either in the same composition or as separate compositions.

For example, EGFL7 antagonists used to treat angiogenesis associated conditions such as cancer or ocular diseases may be combined with cytotoxic, chemotherapeutic, or anti-angiogenic agents as identified above. In a tumor model, EGFL7 was found to remain in the tracks of regressed tumor vessels after the tumor was treated with an anti-VEGF antibody (see Examples). Not wishing to be bound by a particular theory, it is possible that EGFL7 acts to support EC migration along the existing ECM tracks, and thus assists in tumor vessel regrowth subsequent to an anti-angiogenesis treatment. Therefore, it is desirable to use EGFL7 antagonists in combination with an anti-angiogenic agent to enhance or sensitize the activity of the anti-angiogenic agent. In a preferred embodiment, the EGFL7 antagonist is used in combination with the anti-VEGF antibody bevacizumab to enhance its anti-tumor efficacy.

The effective amounts of the therapeutic agents administered in combination with EGFL7 or agonist or antagonist thereof will be at the physician's or veterinarian's discretion. Dosage administration and adjustment is done to achieve maximal management of the conditions to be treated. For example, for treating hypertension, these amounts ideally take into account use of diuretics or digitalis, and conditions such as hyper- or hypotension, renal impairment, etc. The dose will additionally depend on such factors as the type of the therapeutic agent to be used and the specific patient being treated. Typically, the amount employed will be the same dose as that used, if the given therapeutic agent is administered without EGFL7.

Articles of Manufacture

An article of manufacture such as a kit containing EGFL7 or agonists or antagonists thereof useful for the diagnosis or treatment of the disorders described above comprises at least a container and a label. Suitable containers include, for example, bottles, vials, syringes, and test tubes. The containers may be formed from a variety of materials such as glass or plastic. The container holds a composition that is effective for diagnosing or treating the condition and may have a sterile access port (for example, the container may be an intravenous solution bag or a vial having a stopper pierceable by a hypodermic injection needle). The active agent in the composition is EGFL7 or an agonist or antagonist thereto. The label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use. The article of manufacture may also comprise a second or third container with another active agent as described above.

EGFL7 Antibodies

Some of the most promising drug candidates according to the present invention are antibodies and antibody fragments that may inhibit the production or the gene product of the gene identified herein and/or reduce the activity of the gene products.

Polyclonal Antibodies

Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the EGFL7 polypeptide or a fusion protein thereof. It may be useful to conjugate the immunizing agent to a protein known to be immunogenic in the mammal being immunized. Examples of such immunogenic proteins include, but are not limited to, keyhole limpet hemocyanin, serum albumin, bovine thyroglobulin, and soybean trypsin inhibitor. Examples of adjuvants that may be employed include Freund's complete adjuvant and MPL- TDM adjuvant (monophosphoryl Lipid A or synthetic trehalose dicorynomycolate). The immunization protocol may be selected by one skilled in the art without undue experimentation.

Monoclonal Antibodies

The anti-EGFL7 antibodies may, alternatively, be monoclonal antibodies. Monoclonal antibodies may be prepared using hybridoma methods, such as those described by Kohler and Milstein, *Nature* 256:495 (1975). In a hybridoma method, a mouse, hamster, or other appropriate host animal is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the EGFL7 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, *Monoclonal Antibodies: Principles and Practice* (New York: Academic Press, 1986), pp. 59-103. Immortalized cell lines are usually transformed mammalian cells, particularly myeloma cells of rodent, bovine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high-level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. Kozbor, *J. Immunol.* 133:3001 (1984); Brodeur et al., *Monoclonal Antibody Production Techniques and Applications* (Marcel Dekker, Inc.: New York, 1987) pp. 51-63.

The culture medium in which the hybridoma cells are cultured can then be assayed for the presence of monoclonal antibodies directed against the EGFL7 polypeptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.* 107:220 (1980).

After the desired hybridoma cells are identified, the clones may be subcloned by limiting dilution procedures and grown by standard methods. Goding, supra. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy- and light-chain constant domains in place of the homologous murine sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using routine techniques known in the art.

Human and Humanized Antibodies

The anti-EGFL7 antibodies may further comprise humanized antibodies or human antibodies. Humanized forms of non-human (e.g., murine) antibodies are chimeric immunoglobulins, immunoglobulin chains, or fragments thereof (such as Fv, Fab, Fab', F(ab')$_2$, or other antigen-binding subsequences of antibodies) that contain minimal sequence derived from non-human immunoglobulin. Humanized antibodies include human immunoglobulins (recipient antibody) in which residues from a CDR of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin, and all or substantially all of the FR regions are those of a human immunoglobulin consensus sequence. The humanized antibody preferably also will comprise at least a portion of an immunoglobulin constant region (Fc), typically that of a human immunoglobulin. Jones et al., *Nature* 321:522-525 (1986); Riechmann et al., *Nature* 332:323-329 (1988); Presta, *Curr. Op. Struct. Biol.* 2:593-596 (1992).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature* 321:522-525 (1986); Riechmann et al., *Nature* 332:323-327 (1988); Verhoeyen et al., *Science* 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries. Hoogenboom and Winter, *J. Mol. Biol.* 227:381 (1991); Marks et al., *J. Mol. Biol.* 222:581 (1991). The techniques of Cole et al. and Boerner et al. are also available for the preparation of human monoclonal antibodies. Cole et al., *Monoclonal Antibodies and Cancer Therapy*, Alan R. Liss, p. 77 (1985) and Boerner et al., *J. Immunol.* 147(1):86-95 (1991). Similarly, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; and 5,661,016, and in the following scientific publications: Marks et al., *Bio/Technology* 10:779-783 (1992); Lonberg et al., *Nature* 368:856-859 (1994); Morrison, *Nature*, 368:812-813 (1994); Fishwild et al., *Nature Biotechnology* 14:845-851 (1996); Neuberger, *Nature Biotechnology* 14:826 (1996); Lonberg and Huszar, *Intern. Rev. Immunol.* 13:65-93 (1995).

Bispecific Antibodies

Bispecific antibodies are monoclonal, preferably human or humanized, antibodies that have binding specificities for at least two different antigens. In the present case, one of the binding specificities is for the EGFL7 polypeptide, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities. Milstein and Cuello, *Nature* 305:537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.* 10:3655-3659 (1991).

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies, see, for example, Suresh et al., *Methods in Enzymology* 121:210 (1986).

Heteroconjugate Antibodies

Heteroconjugate antibodies are composed of two covalently joined antibodies. Such antibodies have, for example, been proposed to target immune-system cells to unwanted cells (U.S. Pat. No. 4,676,980), and for treatment of HIV infection. WO 91/00360; WO 92/200373; EP 03089. It is contemplated that the antibodies may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate and those disclosed, for example, in U.S. Pat. No. 4,676,980.

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, WO94/11026.

In another embodiment, the antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

Immunoliposomes

The antibodies disclosed herein may also be formulated as immunoliposomes. Liposomes containing the antibody are prepared by methods known in the art, such as described in Epstein et al., *Proc. Natl. Acad. Sci. USA* 82:3688 (1985); Hwang et al., *Proc. Natl. Acad. Sci. USA* 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257:286-288 (1982) via a disulfide-interchange reaction. A chemotherapeutic agent (such as Doxorubicin) is optionally contained within the liposome. See, Gabizon et al., *J. National Cancer Inst.* 81(19):1484 (1989).

Pharmaceutical Compositions of Antibodies

Antibodies specifically binding an EGFL7 polypeptide identified herein, as well as other molecules identified by the screening assays disclosed hereinbefore, can be administered for the treatment of various disorders as noted above and below in the form of pharmaceutical compositions.

The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Methods of Treatment Using the Antibody

It is contemplated that the antibodies to an EGFL7 polypeptide may be used to treat various angiogenesis associated conditions as noted above.

The antibodies are administered to a mammal, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous administration of the antibody is preferred.

Other therapeutic regimens may be combined with the administration of the antibodies of the instant invention as noted above. For example, if the antibodies are to treat cancer, the patient to be treated with such antibodies may also receive radiation therapy. Alternatively, or in addition, a chemotherapeutic agent may be administered to the patient. Preparation and dosing schedules for such chemotherapeutic agents may be used according to manufacturers' instructions or as determined empirically by the skilled practitioner. Preparation and dosing schedules for such chemotherapy are also described in *Chemotherapy Service*, Ed., M. C. Perry (Williams & Wilkins: Baltimore, Md., 1992). The chemotherapeutic agent may precede, or follow administration of the antibody, or may be given simultaneously therewith. The antibody may be combined with an anti-estrogen compound such as tamoxifen or EVISTA™ or an anti-progesterone such as onapristone (see, EP 616812) in dosages known for such molecules.

If the antibodies are used for treating cancer, it may be desirable also to administer antibodies against other tumor-associated antigens, such as antibodies that bind to one or more of the ErbB2, EGFR, ErbB3, ErbB4, or VEGF receptor(s). These also include the agents set forth above. Also, the antibody is suitably administered serially or in combination with radiological treatments, whether involving irradiation or administration of radioactive substances. Alternatively, or in addition, two or more antibodies binding the same or two or more different antigens disclosed herein may be co-administered to the patient. Sometimes, it may be beneficial also to administer one or more cytokines to the patient. In a preferred embodiment, the antibodies herein are co-administered with a growth-inhibitory agent. For example, the growth-inhibitory agent may be administered first, followed by an antibody of the present invention. However, simultaneous administration or administration of the antibody of the present invention first is also contemplated. Suitable dosages for the growth-inhibitory agent are those presently used and may be lowered due to the combined action (synergy) of the growth-inhibitory agent and the antibody herein.

In one embodiment, vascularization of tumors is attacked in combination therapy. The anti-EGFL7 antibody and another antibody (e.g., anti-VEGF) are administered to tumor-bearing patients at therapeutically effective doses as determined, for example, by observing necrosis of the tumor or its metastatic foci, if any. Additional anti-tumor agents can be further administered, such as alpha-, beta-, or gamma-interferon, anti-HER2 antibody, heregulin, anti-heregulin antibody, D-factor, interleukin-1 (IL-1), interleukin-2 (IL-2), granulocyte-macrophage colony stimulating factor (GM-CSF), or agents that promote microvascular coagulation in tumors, such as anti-protein C antibody, anti-protein S antibody, or C4b binding protein (see, WO 91/01753, published 21 Feb. 1991), or heat or radiation.

In other embodiments, a FGF or PDGF antagonist, such as an anti-FGF or an anti-PDGF neutralizing antibody, is administered to the patient in conjunction with the anti-EGFL7 antibody. Treatment with anti-EGFL7 antibodies preferably may be suspended during periods of wound healing or desirable neovascularization.

For the prevention or treatment of cardiovascular, endothelial, and angiogenic disorder, the appropriate dosage of an antibody herein will depend on the type of disorder to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

For example, depending on the type and severity of the disorder, about 1 μg/kg to 50 mg/kg (e.g., 0.1-20 mg/kg) of antibody is an initial candidate dosage for administration to the patient, whether, for example, by one or more separate administrations, or by continuous infusion. A typical daily or weekly dosage might range from about 1 μg/kg to 100 mg/kg or more, depending on the factors mentioned above. For repeated administrations over several days or longer, depending on the condition, the treatment is repeated or sustained until a desired suppression of disorder symptoms occurs. However, other dosage regimens may be useful. The progress of this therapy is easily monitored by conventional techniques and assays, including, for example, radiographic tumor imaging.

Articles of Manufacture with Antibodies

An article of manufacture containing a container with the antibody and a label is also provided. Such articles are described above, wherein the active agent is an anti-EGFL7 antibody.

Diagnosis and Prognosis of Tumors Using Antibodies

If the indication for which the antibodies are used is cancer, while cell-surface proteins, such as growth receptors over expressed in certain tumors, are excellent targets for drug candidates or tumor (e.g., cancer) treatment, the same proteins along with EGFL7 polypeptides find additional use in the diagnosis and prognosis of tumors. For example, antibodies directed against the EGFL7 polypeptides may be used as tumor diagnostics or prognostics.

For example, antibodies, including antibody fragments, can be used qualitatively or quantitatively to detect the expression of genes including the gene encoding the EGFL7 polypeptide. The antibody preferably is equipped with a detectable, e.g., fluorescent label, and binding can be monitored by light microscopy, flow cytometry, fluorimetry, or other techniques known in the art. Such binding assays are performed essentially as described above.

In situ detection of antibody binding to the marker gene products can be performed, for example, by immunofluorescence or immunoelectron microscopy. For this purpose, a histological specimen is removed from the patient, and a labeled antibody is applied to it, preferably by overlaying the antibody on a biological sample. This procedure also allows for determining the distribution of the marker gene product in the tissue examined. It will be apparent to those skilled in the art that a wide variety of histological methods are readily available for in situ detection.

The following Examples are offered for illustrative purposes only, and are not intended to limit the scope of the present invention in any way.

The disclosures of all patent and literature references cited in the present specification are hereby incorporated by reference in their entirety.

EXAMPLES

Commercially available reagents referred to in the Examples were used according to manufacturer's instructions unless otherwise indicated. The source of those cells identified in the following Examples, and throughout the specification, by ATCC accession numbers is the American Type Culture Collection, Manassas, Va. 20108.

All references cited herein are hereby incorporated by reference.

Example 1

Cloning of EGFL7

EGFL7 was identified and cloned in an effort to discover novel human secreted and transmembrane proteins, particularly those involved in the regulation of vascular development. Details of the cloning and expression of human EGFL7 are described in, for example, patent application US20030224948A1 (wherein EGFL7 is identified as PRO1449). Briefly, whole mount in situ hybridization screens were performed to identify secreted factors and receptors that are enriched in mouse embryonic vasculatures. By way of signal sequence prediction and extracellular domain homology searching, hundreds of human and mouse cDNAs representing putative secreted factors and receptors were identified and collected. Using the mouse cDNAs as templates, riboprobes were generated and in situ hybridizations were performed on whole mouse embryos ranging from E7.5 to E14.5. This developmental time window was chosen because it encompasses many key stages in vasculogenesis and angiogenesis. Among many genes identified from this screen, EGFL7 is uniquely expressed in the endothelia of actively growing blood vessels. See expression details below.

Figures 1, 1B:
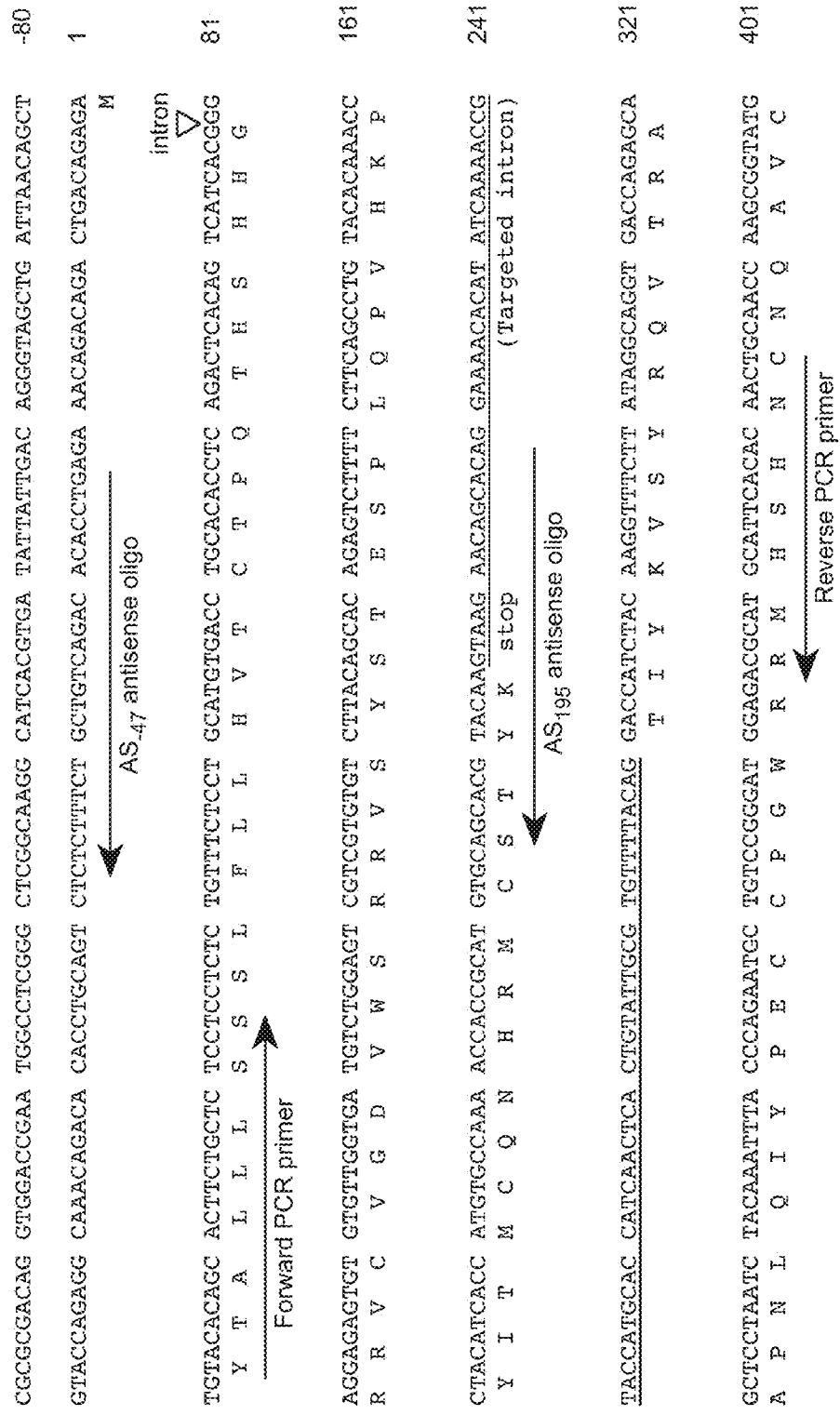

*Xenopus* EGFL7 was identified as a rough draft derived from a single genbank entry BC044267. Zebrafish EGFL7 was cloned by low stringency PCR and subsequent screening of a cDNA library made from 24 hpf embryos, based on the homology among three known species (human, mouse and *xenopus*). The sequences of zebrafish EGFL7 cDNA, partial genomic DNA and amino acid are shown in FIG. 1B. EGFL8 was identified by BLAST using EGFL7 sequences.

Radiation hybrid mapping experiments using the T51 panel placed the zebrafish EGFL7 in linkage group 21 (LG21), close to the EST marker flc20d12.y1 (Accession number AW566846). This region of zebrafish LG21 appears to be syntenic with human chromosome 9q33 to 9q34, the locus where human EGFL7 resides. The following genes are found within this human locus: Notch1 (9q34), carboxyl ester lipase (CELL; 9q34), and proteasome subunit beta 7 (psmb7; 9q33). These genes are present in the region of LG21 where zebrafish EGFL7 mapped (LG21, 19.6-29.0 CM).

The EGFL7 gene encodes a putative secreted protein with a relative molecular mass of ~30 kD. EGFL is evolutionary conserved. See FIG. 1a. The human (*Homo sapiens*) amino acid sequence shares 77.45%, 47.12% and 42.96% homology to that of the mouse (*Mus musculus*), xenopus (*Xenopus laevis*) and zebrafish (*Danio rerio*), respectively.

The EGFL7 protein contains a signal sequence, an EMI domain at the N-terminus (EMI domain is present in a number of extracellular matrix associated proteins involved in regulating cell adhesion), followed by two EGF-like domains and a leucine and valine rich C-terminal region. The mammalian EGFL7 belongs to a small gene family. BLAST searches identified one closely related gene EGFL8, which has an identical domain organization as EGFL7. Interestingly, this gene family appears to be more complex in mammals, since no EGFL8 orthologue has been identified in several fish genomes (*Danio rerio, Medaka* and *Fugu*).

The cDNA encoding human EGFL7 was deposited under the terms of the Budapest Treaty with the American Type Culture Collection, 10801 University Blvd., Manassas, Va. 20110-2209, USA (ATCC), with ATCC Deposit No. 203243 (deposited on Sep. 9, 1998).

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between the assignee of the present application and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Example 2

Expression of EGFL7

To elucidate the expression pattern of EGFL7, whole mount in situ hybridization, immunofluorescent staining and radioactive in situ hybridization were carried out on mouse and zebrafish embryos as well as mouse and human tissue sections.

Zebrafish and Mouse Strains

Mouse embryos were harvested from timed-pregnant CD-1 mice. Tüebingen long fin (TL) wild-type zebrafish line, ~30 hpf cloche (clo$^{m39}$) homozygous mutant embryos and their wild-type siblings were used in the expression and activity studies described herein below. Adult zebrafish and embryos were maintained as previously described (Westerfield 1993 Zebrafish Book).

Radioactive In Situ Hybridization

Tissues were processed for in situ hybridization by a method described previously. Phillips et al. (1990) *Science* 250:290-4. $^{33}$P-UTP-labelled RNA probes were generated as described. Melton et al. (1984) *Nucleic Acids Research* 12:7035-56. EGFL7 sense and antisense probes were synthesized from two human cDNAs and one murine cDNA that correspond to nucleotides 382 to 1062, −137 to 150, and 173 to 774, respectively. (Nucleotide A in the initiation codon is counted as nucleotide #1).

Wholemount In Situ Hybridizations

Wholemount in situ hybridizations were carried out as described with slight modifications. Shimamura et al. *Development* 120:2225-2234 (1994). Stained embryos were cleared in a 2:1 mixture of benzyl alcohol/benzyl benzoate for photography. Sense and antisense riboprobes were made using the following templates: a murine EGFL7 partial cDNA clone (IMAGE clone 519249, Genbank accession: AA107358); a zebrafish EGFL7 partial cDNA clone corresponding to nucleotides 169 to 807; all other molecular markers were from the Fishman (MGH), Stainier (UCSF) and Weinstein (NIH) labs. Following whole-mount in situ hybridization analysis, embryos were re-fixed in 4% paraformaldehyde (PFA) in 1×PBS, dehydrated through an ethanol series, and embedded in JB-4Plus plastic (Polysciences). 5 μm sections were counterstained with 0.2% nuclear fast red, and mounted in Cytomount 60.

AP Staining

Endogenous alkaline phosphatase activity in 48 hpf wholemount zebrafish embryos was detected as described previously. Childs et al. *Development* 129:973-982 (2002).

Deconvolution Microscopy

Embryos were fixed overnight at 4° C. in 4% PFA, cryoprotected in 20% sucrose/PBS, snap frozen in 7.5% gelatin/15% sucrose and sectioned. Slides were air dried, permeabilized in 1×PBS/0.1% Triton X-100/1% DMSO, blocked for 20 min in the above solution plus 1% BSA, stained with 66 nM ALEXA Fluor594-phalloidin (Molecular Probes) for 20 min, washed, mounted with Vectashield DAPI (Vector labs.) and analyzed using a Deltavision Deconvolution Microscope with 60× oil objective.

Immunofluorescent Staining

Armenian hamsters were immunized with recombinant murine EGFL7 protein expressed in *E. coli*. Monoclonal antibodies were generated by hybridoma fusion and subcloning. Two monoclonal antibodies 1C8 and 5H7 that recognize different epitopes were used for immunofluorescent staining. Mouse tissues were snap frozen and cryosectioned. Fixed cells or 5 μm unfixed tissue sections were stained as described. Parker et al. *Methods in Cell Biology* 59:313-36 (1999). Antibodies used in this study are: Anti-ZO-1 mab (Zymed Inc. Cat. #33-9100); anti-GFP (Torrey Pines Biolabs, Cat. # TP401); anti-vinculin mab (Sigma).

Results

Figure 2C:
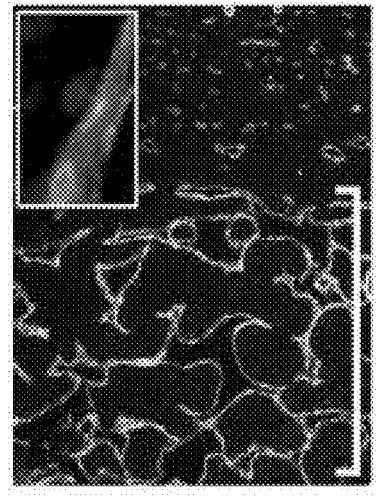
FIGS. 2a-2n depict EGFL7 expression profile. EGFL7 whole mount in situ hybridization on mouse (a-b) and zebrafish (j-n) embryos. b: cross-section of a stained with nuclear-fast-red. RBC=red blood cells. j-m: light arrow=lateral plate mesoderm, dark arrow=dorsal aorta, dark arrowhead=ISVs. Inset: close-up of the trunk. n: cloche mutant. so=somite. c: pregnant mouse uterus stained for EGFL7 and PECAM. Bracket=decidua. d-i: Radioactive in situ hybridization (g-i) and H&E (d-f) on human lung sections. Scale bar: 0.45 mm (a, m, n), 0.07 mm (b), 0.38 mm (c-i), 0.25 mm (j, l), 0.15 mm (k), 0.26 mm (m inset), and 0.04 mm (c inset).
Figure 2B:
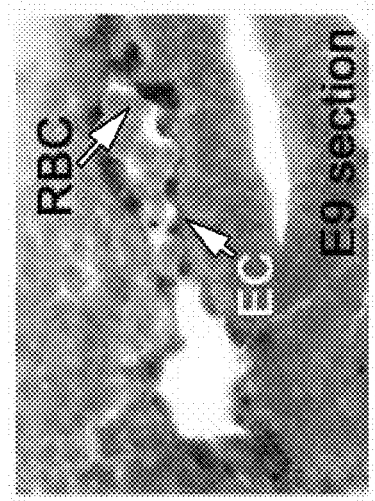
Figure 2A:
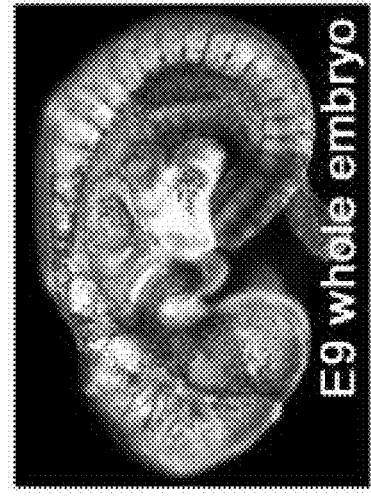
Figure 2F:
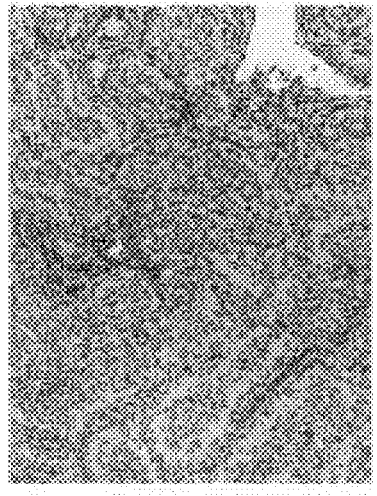
Figure 2E:
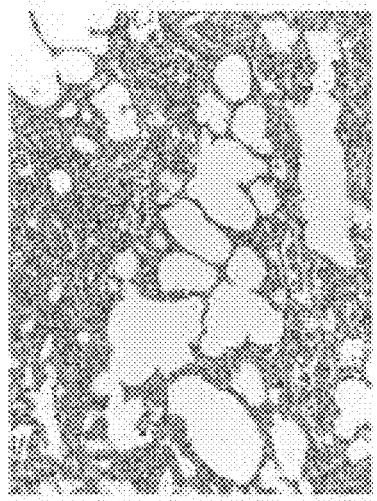

The expression pattern of EGFL7 is conserved across species, In mouse, human and zebrafish embryos, high levels of EGFL7 transcripts were detected in endothelial progenitors and ECs in all vessels (FIGS. 2a, 2b, 2g, 2j-2m), as well as the endocardium. Strong vascular expression persisted throughout embryonic and neonatal development; however, the message was undetectable in many adult organs (FIG. 2h). In adult mice, a few highly vascularized organs such as the lung, heart and kidney continued to express EGFL7 in a small subset of vessels. Interestingly, EGFL7 expression was strongly up regulated in many proliferative tissues including tumors (FIG. 2i), reproductive organs during pregnancy (FIG. 2c), and inflamed tissues. Moreover, strong EGFL7 expressions were found in primary human disease tissues including, but not limited to, lung adenocarcinoma and sqamous cell carcinoma, renal cell carcinoma, prostate carcinoma, ovarian carcinoma, hepatic carcinoma, gastric carcinoma, chondrosarcoma, osterosarcoma, neovascular membranes from diseased eyes and sites of inflammation.

This unique expression pattern suggests that high levels of EGFL7 are associated with vascular growth and remodeling. EGFL7 was not detected outside of the cardiovascular and hematopoietic systems, this observation was confirmed by the fact that EGFL7 expression is completely abolished in the avascular zebrafish mutant cloche (FIG. 2n). Stainier et al. *Dev. Suppl.* 121:3141-3150 (1995).

Immunofluorescence staining shows that the EGFL7 protein is secreted but remains in the vicinity of the ECs (inset of FIG. 2c), apparently associated with the extracellular matrix. Further study using a tumor model treated with an anti-VEGF antibody showed that after tumor vasculature became fragmented due to the anti-VEGF treatment, EGFL7 remained in the ECM tracks of the regressed tumor vessels. This may suggest a potentially important role of EGFL7 in supporting tumor vessels to eventually grow back and thus "escape" the anti-VEGF treatment.

Example 3

Phenotypic Analysis of Animals with Reduced EGFL7 Activity

A. Vascular Defects in the EGFL7 Knockdown Zebrafish

In a recent report, conditioned medium containing the recombinant EGFL7 protein is shown to inhibit smooth muscle cell (SMC) migration in vitro. Soncin et al. *EMBO J.* 22:5700-5711 (2003). However, its in vivo function has not been defined. To uncover the in vivo biological function of EGFL7, the model organism zebrafish was used because of the availability of tools to study vasculogenesis and angiogenesis, and the ease to manipulate gene expression in embryos. Fishman et al. *Circulation Research* 74:757-63 (1994); Weinstein et al. *Cardiovascular Research* 31:E17-24 (1996); Dooley et al. *Current Opinion in Genetics & Development* 10:252-6 (2000); Nasevicius & Ekker *Nature Genetics* 26:216-20 (2000). Furthermore, it was found that Egfl8 was expressed in a subset of blood vessels and peripheral nerves in mouse embryos, making it a potential redundant factor for EGFL7. On the other hand, no Egfl8 orthologue has been found in zebrafish and several other fish genomes. Therefore, zebrafish provides a unique tool for defining the biological function of this gene family.

Gene knockdown experiments were performed using two different morpholino antisense oligos targeting the zebrafish EGFL7: oligo $AS_{47}$ hybridizes to the 5' UTR and blocks translation; oligo $AS_{195}$ hybridizes with an exon-intron junction, resulting in intron retention and hence premature translation termination. Positions of the two antisense oligos are indicated in FIG. 1B. Randomized controls are

```
CON(-47): ACGACGGTCACGATGAA TGGAGAGT;
and

CON(195): CATTGTTCATCGTCTTGTTGCGTGT.
```

A fluorescein tag was added to aid in identifying embyros that were properly injected and to confirm uniform distribution of the oligonucleotides in developing embryos. 5 mM oligo stock solution (~40 mg/ml) in water was diluted in 1× Danieu's solution (58 mM NaCl, 0.7 mM KCl, 0.4 mM $MgSO_4$, 5 mM HEPES, pH 7.6) with 0.25% phenol red. A bolus of approximately 4.6 nl was injected into each 1-cell to 8-cell stage embryo using a Drummond Nanoject microinjector. Titration experiments revealed that injection of 4 ng antisense oligo per embryo caused specific vascular defects with no observable defects in other structures, along with no significant increase in mortality in the randomized control oligo-injected embryos.

Both oligos gave identical phonotypical results. When examined after the onset of circulation [~24 hours post fertilization (hpf)], more than 40% of the EGFL7 knockdown embryos (KDs) showed overt signs of vascular defects: they either have no circulation at all, or develop an incomplete circulatory loop; many have pericardial edema and hemorrhage (FIG. 3a). In contrast, only 3% of the control oligo injected fish have minor vascular defects.

Furthermore, expression patterns of several vascular endothelial markers were analyzed, including fli1, flk1, tie1, ephrinB2, and gridlock (arterial EC marker), flt4 and EphB4 (venous EC marker), and endogenous alkaline phosphatase activity. Brown et al. *Mech. Dev.* 90:237-252 (2000); Fouquet et al. *Dev. Biol.* 183:37-48 (1997); Liao et al. *Development* 124:381-389 (1997); Lyons et al. *Dev. Dyn.* 212:133-140 (1998); Lawson & Weinstein *Nature Rev. Genet.* 3:674-682 (2002); Zhong et al. *Science* 287:1820-1824 (2000); Childs et al. *Development* 129:973-982 (2002). Knockdown experiments were also carried out in a flk1-promoter-GFP transgenic line. From the 7-somite stage to 30 hpf, the overall spatial distribution and intensity of the above markers were unaffected in the KDs, furthermore, all primary arteries and veins were formed in the correct locations in the KDs (FIGS. 3,4), indicating that there is no significant defect in early EC differentiation, proliferation and migration. However, tubulogenesis throughout the entire system was disrupted in the KDs. At 30 hpf, many primary vessels in the KDs had either disorganized lumens or no lumen at all (FIG. 3c-d, 3h). The prevalence of the tubulogenesis defect displayed by molecular markers is between 75 and 85% in multiple experiments. For instance, fli1 staining at 30 hpf revealed that 76% (28/37) of the KDs had tubulogenesis defect, whereas all control embryos (n=37) developed normal vascular tubes. To confirm the knockdown specificity, the vascular phenotype caused by $AS_{-47}$ was rescued by the EGFL7 coding RNA without the 5' untranslated region.

Lack of lumen formation in the EGFL7 KDs was verified by the finding that major vessels in these embryos could not be filled with dye. Although it is possible that the tubulogenesis defect is a consequence of vascular collapse due to lack of blood flow, the following observations make it unlikely: first, cardiac contractile function was normal in the EGFL7 KDs; second, primary vessel lumen formation and short term maintenance were normal in the silent heart mutants that lack circulation. Sehnert et al. *Nature Genet.* 31:106-110 (2002); Isogai et al. *Development* 130:5281-5290 (2003).

Figure 2D:
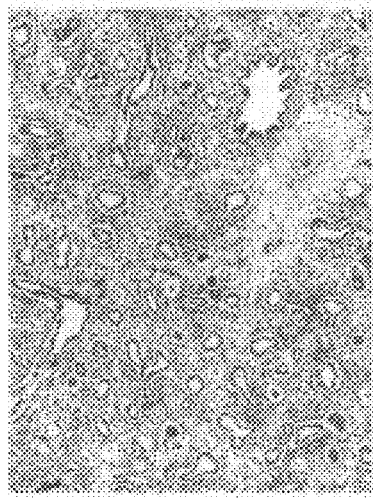

The EGFL7 KD animals also showed progressive angiogenesis defects. The initial sprouting of intersegmental vessels (ISVs) occurred normally in the mutants at 22-24 hpf (FIG. 3b). However, these secondary vessels gradually disappeared, as the ISVs were partially missing at 30 hpf (FIG. 2c-d), and were completely eliminated by 48-72 hpf. It is likely that lack of circulation partly contributes to the angiogenesis defect, since it is documented that ISVs undergo regression in the absence of blood flow. Isogai et al. *Development* 130:5281-5290 (2003). Due to the dominant phenotype in the primary vessels, the exact role of EGFL7 in angiogenesis can be further defined using methods such as inducible knockout.

Because vascular development is dependent on neighboring tissues, question remains as to whether the vascular defect seen in the EGFL7 KDs is an indirect consequence of disrupting surrounding tissues. Brown et al. *Mech. Dev.* 90:237-

252 (2000); Sumoy et al. *Mech. Dev.* 63:15-27 (1997); Vokes & Krieg *Dev. Suppl.* 129:775-785 (2002). In cross sections of the KDs, a normal complement of tissues appear to exist (FIG. 3). Furthermore, in situ hybridization with fkd7, ntl, axial/fkd1 and gata1 illustrated that all axial structures and the hematopoietic lineage developed normally in the KDs. Odenthal & Nusslein-Volhard *Dev. Genes Evol.* 208:245-258 (1998); Schulte-Merker et al. *Development* 116:1021-1032 (1992); Strahle et al. *Genes Dev.* 7:1436-1446 (1993); Parker et al. *Methods Cell Biol.* 59:313-336 (1999). After the onset of circulation, gata1$^+$ cells in the KDs remained in the posterior ventrolateral region of the embryo where they initially developed, confirming that the vasculature is defective. Finally, defective recruitment of SMC is an unlikely causative factor since there was no evidence of perivascular SM22A expression in wild type embryos at the 26-somite stage, a time point when the vascular defects were obvious in the KDs. Taken together, the data suggests that failure of vascular tubulogenesis is a primary defect caused by EGFL7 knockdown.

Since EC number dictates vascular morphogenesis, further observation focused on whether EC number was altered in the EGFL7 KDs. Fong et al. *Development* 126:3015-3025 (1999). Serial cross sections showed that knocking down EGFL7 did not change the total number of ECs at all axial levels regardless of developmental stage (FIG. 4). Furthermore, based on ephrinB2 and flt4 expression, and the differential regulation of flk1 promoter between artery and vein in the flk1:GFP embryos, arterial and venous EC numbers were also found to be unaffected (FIG. 4). In contrast to EGFL7, knocking down vegf, a known mitogenic factor for EC, reduced EC number significantly, and subsequently disrupted tube formation. Thus, the data indicates that EGFL7 plays a unique role that is distinctive from VEGF and is mainly required during vascular tubulogenesis.

In order to describe the vascular phenotype at a cellular level, a time course analysis was carried out using the flk1: GFP fish. Serial cross sections of the trunk and longitudinal sections of the head were taken at the 22-, 24-, 26-somite (before circulation), 24 hpf (onset of circulation), and 30 hpf stages. Analyses of these sections reveal a series of cellular events during the cord-to-tube transition in the control embryos. At the 22-somite stage, arterial and venous angioblasts coalesced into single cords. Extensive tight junctions revealed intimate connections among angioblasts. Around the 24-somite stage, gradual separation of angioblasts was evident by substantial refinement of tight junctions. By the 26-somite stage, angioblasts were sufficiently segregated, such that arterial and venous angioblasts occupied distinct domains and aligned in the form of rudimentary tubes. Subsequently, ECs underwent extensive morphological changes and became squamous, thereby rendering the vascular tubes their final shape. This sequence of events leading to the formation of major vascular tubes was severely impaired in the EGFL7 KDs. At all the stages examined, the knockdown angioblasts failed to separate and retain extensive tight junctions. They also failed to change shape at the later stages (FIG. 4*h*).

B. Reduced Tumor Growth and Defective Vasculature in the EGFL7 Knockout Mice

To further elucidate EGFL7's function in mammalian animals, mEGFL7 knockout (KO) mice were generated and used as host animals for tumor implants. The KO mice were originally generated in a 129/BL6 background, and have been backcrossed to BL6. Animals used in the experiment were 3 to 4 generation backcrossed.

Over 500,000 B16(F10) melanoma tumor cells were injected subcutaneously in the dorsal flank of each animal. Injection sites were examined daily for tumor incidence. Tumors were measured regularly to determine growth rate. The tumor growth rate of EGFL7$^{-/-}$ homozygous animals were compared with that of EGFL7$^{+/-}$ heterozygous or wild-type littermates.

As shown in FIGS. 6 and 7, B16 melanoma tumor growth was significantly reduced in animals with complete knockout of EGFL7.

A similar tumor growth study using Lewis lung carcinoma (LLC) tumor implants also showed reduced tumor growth in homozygous EGFL7$^{-/-}$ KO mice. Furthermore, LLC tumors in a subset of EGFL7$^{-/-}$ KO mice failed to vascularize, implicating EGFL7's role in tumor vasculargenesis.

A study comparing retinal vasculature formation in the EGFL7$^{-/-}$ KO mice versus the wild type mice showed that lack of EGFL7 function resulted in delayed retinal vascular migration, despite the relative normal retinal formation. Moreover, in the wild type mice, EGFL7 expression was localized to the migration front of retinal development.

Example 4

EGFL7 Supports EC Adhesion and Migration

Failure of EC separation as shown in Example 3 indicates that either EC motility or adhesion is improperly regulated in the EGFL7 KDs. In vitro endothelial cell migration and adhesion assays were carried out to distinguish between these two possibilities.

Plates were coated with 5 μg/cm$^2$ protein [BSA (Sigma), collagen (Upstate), Fibronectin (Sigma), recombinant human EGFL7 produced in *E. coli* at Genentech]. After PBS rinses, HUVEC (Cambrex) were plated at a density of 5×10$^5$/cm$^2$ in EGM2 medium (Cambrex) and centrifuged for 5 min at 140×g to synchronize cell attachment, and then incubated. To analyze specificity, plates were pre-incubated with the indicated concentrations of antibody prior to HUVEC plating.

Monoclonal anti-human EGFL7 antibodies were generated using the recombinant human and mouse EGFL7 polypeptides as immunogen. Antibody-antigen bindings were evaluated by ELISA. The blocking activities of these antibodies were tested in assays such as the HUVEC adhesion assay. Initial assays identified anti-EGFL7 Mabs from hybridoma 10G9, 18F7, 3A5 and 1B12 as having the strongest inhibitory activity.

To determine adhesion strength, inverted plates were centrifuged at 46, 183 or 411×g after 60 min of incubation. The number of adherent cells was quantified using a fluorescence-based assay (CyQUANT, Molecular probes) and readouts were taken using a fluorescence plate reader (Spectramax, Molecular Devices).

Figure 5F:
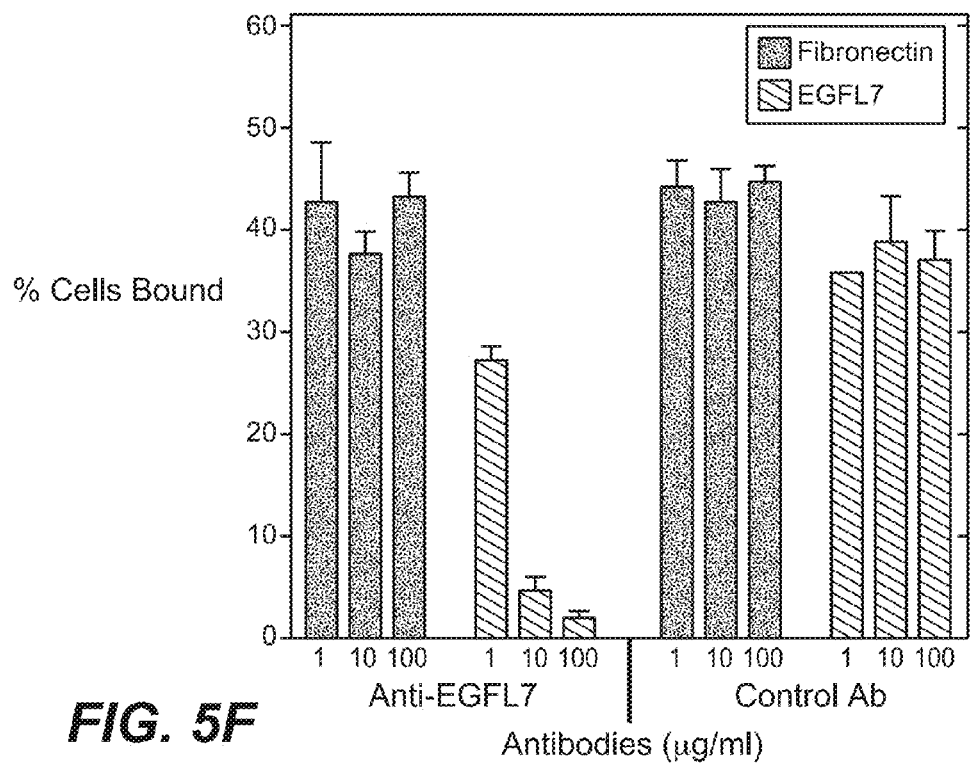
Figure 5G:
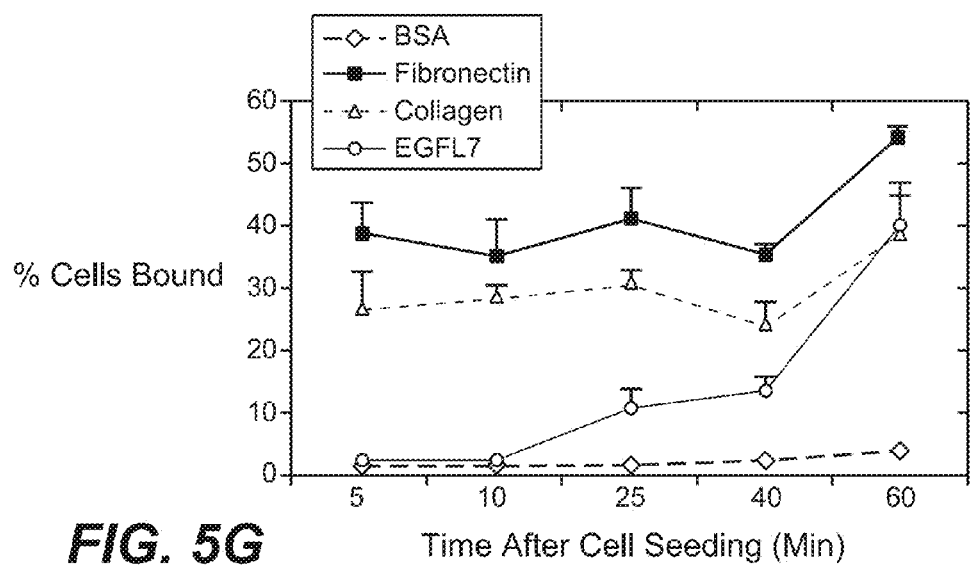

The results showed that EGFL7 coated on culture plates enhanced HUVEC adhesion (FIG. 5). Interestingly, the strength of adhesion promoted by EGFL7 was significantly weaker than other classic cell adhesion molecules such as fibronectin and collagens (FIG. 5*e*). Moreover, the kinetics of HUVEC adhesion to EGFL7 was much slower than other substrates (FIG. 5*g*). Taking into account the EGFL7 expression pattern, subcellular localization, in vivo function, and cell adhesion properties, it is suggested that during active vascular growth, EGFL7 may provide a permissive substrate that favors motility over stable attachment, thereby enabling the local movement of angioblasts that is required for tube formation. Furthermore, migration assays using EGFL7 coated substrates with or without blocking anti-EGFL7 Mabs showed that EGFL7 substrate support HUVEC migration.

An in vitro tube formation assay in the presence of selected anti-EGFL7 Mabs showed that some of the blocking antibodies, including those from hybridoma 18F7, 3A5, 10G9 and 1B12, significantly altered in vitro tube formation, further supporting the critical role of EGFL7 during vascular formation.

The foregoing written specification is considered to be sufficient to enable one skilled in the art to practice the invention. However, various modifications of the invention in addition to those shown and described herein will be apparent to those skilled in the art from the foregoing description and fall within the scope of the appended claims.

What is claimed is:

1. A method of reducing or inhibiting angiogenesis in a subject having a pathological condition associated with angiogenesis, comprising administering to the subject an EGFL7 antagonist capable of interfering with EGFL7-induced vascular tube formation, thereby reducing or inhibiting angiogenesis in the subject, wherein the EGFL7 antagonist is an anti-EGFL7 antibody.

2. The method of claim 1, wherein the pathological condition is a neoplasm.

3. The method of claim 2, wherein the neoplasm is a carcinoma.

4. The method of claim 1, wherein the pathological condition is associated with the eye.

5. The method of claim 4, wherein the pathological condition is an intraocular neovascular disease.

6. The method of claim 1, further comprising administering to the subject an anti-angiogenic agent.

7. The method of claim 6, wherein the anti-angiogenic agent is administered prior to or subsequent to the administration of the EGFL7 antagonist.

8. The method of claim 6, wherein the anti-angiogenic agent is administered concurrently with the EGFL7 antagonist.

9. The method of claim 6, wherein the anti-angiogenic agent is an antagonist of vascular endothelial cell growth factor (VEGF).

10. The method of claim 9, wherein the VEGF antagonist is an anti-VEGF antibody.

11. The method of claim 10, wherein the anti-VEGF antibody is bevacizumab.

12. The method of claim 1, wherein the EGFL7 antagonist's ability to interfere with EGFL7-induced endothelial cell migration is detected in an in vitro cell migration assay.

13. A method of enhancing efficacy of an anti-angiogenic agent in a subject having a pathological condition associated with angiogenesis, comprising administering to the subject an EGFL7 antagonist in combination with the anti-angiogenic agent capable of inhibiting angiogenesis, thereby enhancing said anti-angiogenic agent's inhibitory activity, wherein the EGFL7 antagonist is an anti-EGFL7 antibody capable of interfering with EGFL7-induced vascular tube formation.

14. The method of claim 13, wherein the pathological condition is a neoplasm.

15. The method of claim 14, wherein the neoplasm is a carcinoma.

16. The method of claim 13, wherein the pathological condition is associated with the eye.

17. The method of claim 16, wherein the pathological condition is an intraocular neovascular disease.

18. The method of claim 15, further comprising administering a chemotherapeutic agent.

* * * * *

SEQUENCE LISTING

<160> NUMBER OF SEQ ID NOS: 11

<210> SEQ ID NO 1
<211> LENGTH: 273
<212> TYPE: PRT
<213> ORGANISM: Homo sapiens

<400> SEQUENCE: 1

Met Arg Gly Ser Gln Glu Val Leu Leu Met Trp Leu Leu Val Leu
 1               5                  10                  15

Ala Val Gly Gly Thr Glu His Ala Tyr Arg Pro Gly Arg Arg Val
                20                  25                  30

Cys Ala Val Arg Ala His Gly Asp Pro Val Ser Glu Ser Phe Val
                35                  40                  45

Gln Arg Val Tyr Gln Pro Phe Leu Thr Thr Cys Asp Gly His Arg
                50                  55                  60

Ala Cys Ser Thr Tyr Arg Thr Ile Tyr Arg Thr Ala Tyr Arg Arg
                65                  70                  75

Ser Pro Gly Leu Ala Pro Ala Arg Pro Arg Tyr Ala Cys Cys Pro
                80                  85                  90

Gly Trp Lys Arg Thr Ser Gly Leu Pro Gly Ala Cys Gly Ala Ala
                95                 100                 105

Ile Cys Gln Pro Pro Cys Arg Asn Gly Gly Ser Cys Val Gln Pro
               110                 115                 120

Gly Arg Cys Arg Cys Pro Ala Gly Trp Arg Gly Asp Thr Cys Gln
               125                 130                 135

Ser Asp Val Asp Glu Cys Ser Ala Arg Arg Gly Gly Cys Pro Gln
               140                 145                 150

Arg Cys Ile Asn Thr Ala Gly Ser Tyr Trp Cys Gln Cys Trp Glu
               155                 160                 165

Gly His Ser Leu Ser Ala Asp Gly Thr Leu Cys Val Pro Lys Gly
               170                 175                 180

Gly Pro Pro Arg Val Ala Pro Asn Pro Thr Gly Val Asp Ser Ala
               185                 190                 195

Met Lys Glu Glu Val Gln Arg Leu Gln Ser Arg Val Asp Leu Leu
               200                 205                 210

Glu Glu Lys Leu Gln Leu Val Leu Ala Pro Leu His Ser Leu Ala
               215                 220                 225

Ser Gln Ala Leu Glu His Gly Leu Pro Asp Pro Gly Ser Leu Leu
               230                 235                 240

Val His Ser Phe Gln Gln Leu Gly Arg Ile Asp Ser Leu Ser Glu
               245                 250                 255

Gln Ile Ser Phe Leu Glu Glu Gln Leu Gly Ser Cys Ser Cys Lys
               260                 265                 270

Lys Asp Ser

<210> SEQ ID NO 2
<211> LENGTH: 277
<212> TYPE: PRT
<213> ORGANISM: Mus musculus

<400> SEQUENCE: 2

```
Met Gln Thr Met Trp Gly Ser Gly Glu Leu Leu Val Ala Trp Phe
 1               5                  10                  15

Leu Val Leu Ala Ala Asp Gly Thr Thr Glu His Val Tyr Arg Pro
                20                  25                  30

Ser Arg Arg Val Cys Thr Val Gly Ile Ser Gly Ser Ile Ser
                35                  40                  45

Glu Thr Phe Val Gln Arg Val Tyr Gln Pro Tyr Leu Thr Thr Cys
                50                  55                  60

Asp Gly His Arg Ala Cys Ser Thr Tyr Arg Thr Ile Tyr Arg Thr
                65                  70                  75

Ala Tyr Arg Arg Ser Pro Gly Val Thr Pro Ala Arg Pro Arg Tyr
                80                  85                  90

Ala Cys Cys Pro Gly Trp Lys Arg Thr Ser Gly Leu Pro Gly Ala
                95                 100                 105

Cys Gly Ala Ala Ile Cys Gln Pro Pro Cys Gly Asn Gly Gly Ser
               110                 115                 120

Cys Ile Arg Pro Gly His Cys Arg Cys Pro Val Gly Trp Gln Gly
               125                 130                 135

Asp Thr Cys Gln Thr Asp Val Asp Glu Cys Ser Thr Gly Glu Ala
               140                 145                 150

Ser Cys Pro Gln Arg Cys Val Asn Thr Val Gly Ser Tyr Trp Cys
               155                 160                 165

Gln Gly Trp Glu Gly Gln Ser Pro Ser Ala Asp Gly Thr Arg Cys
               170                 175                 180

Leu Ser Lys Glu Gly Pro Ser Pro Val Ala Pro Asn Pro Thr Ala
               185                 190                 195

Gly Val Asp Ser Met Ala Arg Glu Glu Val Tyr Arg Leu Gln Ala
               200                 205                 210

Arg Val Asp Val Leu Glu Gln Lys Leu Gln Leu Val Leu Ala Pro
               215                 220                 225

Leu His Ser Leu Ala Ser Arg Ser Thr Glu His Gly Leu Gln Asp
               230                 235                 240

Pro Gly Ser Leu Leu Ala His Ser Phe Gln Gln Leu Asp Arg Ile
               245                 250                 255

Asp Ser Leu Ser Glu Gln Val Ser Phe Leu Glu His Leu Gly
               260                 265                 270

Ser Cys Ser Cys Lys Lys Asp
               275
```

<210> SEQ ID NO 3
<211> LENGTH: 280
<212> TYPE: PRT
<213> ORGANISM: Xenopus Laevis

<400> SEQUENCE: 3

```
Met Trp Lys Val Ser Cys Leu Val Thr Gly Tyr Leu Leu Ile Leu
 1               5                  10                  15

Ala Val Thr Ser Ala Ala Asp His Leu Tyr Arg Thr Gly Arg
                20                  25                  30

Arg Ile Cys Ser Ala Asp Gly His Pro Gly Thr Val Ser Val Thr
                35                  40                  45

Gln Ser Phe Val Gln Pro Val His Ser Pro Ile Met Thr Leu Cys
                50                  55                  60
```

```
Glu Gly His Arg Ile Cys Ser Thr Tyr Arg Thr Thr Tyr Lys Val
                65                  70                  75

Ser Tyr Arg Gln Val Ser Arg Lys Thr Ser Phe Pro Leu Tyr Ser
            80                  85                  90

Cys Cys Pro Gly Trp Arg Arg Ile Gly Ala Gln Thr His Ser Cys
        95                 100                 105

Gly Gln Ala Leu Cys Arg Leu Gln Cys Gln Asn Gly Gly Thr Cys
            110                 115                 120

Val Ser Ser Asn Lys Cys Glu Cys Pro Ala Gly Trp Arg Gly Ile
            125                 130                 135

His Cys Gln Met Asp Val Asp Glu Cys Ser Asp Gly Thr His Gln
            140                 145                 150

Cys Ser Gln Ala Cys Ile Asn Ser Ala Gly Ser Phe Ser Cys Glu
            155                 160                 165

Cys Leu Glu Gly Tyr Arg Leu Met Ala Asp Gly Lys Thr Cys Arg
            170                 175                 180

Lys Val Pro Ala Pro Thr Val Pro Pro Ala Ser Pro Thr Ser Val
            185                 190                 195

Gln Glu Ser Gly Ile Pro His Ser Val Lys Glu Glu Met Ala Glu
            200                 205                 210

Leu Arg Ser Lys Ile Asp Val Leu Glu Gln Lys Leu His Leu Leu
            215                 220                 225

Leu Thr Pro Phe Gln Gly Leu Thr Thr Phe Ser Pro Asp Asp Ala
            230                 235                 240

Ala Asp Pro Ile Ala Leu Leu Thr Arg Ser Leu Gln Gln Leu Asp
            245                 250                 255

Arg Ile Asp Ser Leu Ser Glu Gln Ile Ser Phe Leu Glu Glu Arg
            260                 265                 270

Leu Glu Thr Cys Ser Cys Lys Thr Glu Leu
            275                 280

<210> SEQ ID NO 4
<211> LENGTH: 277
<212> TYPE: PRT
<213> ORGANISM: Danio rerio

<400> SEQUENCE: 4

Met Tyr Thr Ala Leu Leu Leu Ser Ser Ser Leu Phe Leu Leu His
 1               5                  10                  15

Val Thr Cys Thr Pro Gln Thr His Ser His Gly Arg Arg Val
            20                  25                  30

Cys Val Gly Asp Val Trp Ser Arg Arg Val Ser Tyr Ser Thr Glu
            35                  40                  45

Ser Phe Leu Gln Pro Val His Lys Pro Tyr Ile Thr Met Cys Gln
            50                  55                  60

Asn His Arg Met Cys Ser Thr Tyr Lys Thr Ile Tyr Lys Val Ser
            65                  70                  75

Tyr Arg Gln Val Thr Arg Ala Ala Pro Asn Leu Gln Ile Tyr Pro
            80                  85                  90

Glu Cys Cys Pro Gly Trp Arg Arg Met His Ser His Asn Cys Asn
            95                 100                 105

Gln Ala Val Cys Glu Gln Ser Cys Ala Asn Gly Gly Ser Cys Val
            110                 115                 120

Arg Pro Asn His Cys Ala Cys Leu Arg Gly Trp Thr Gly Arg Phe
```

```
                    125                 130                 135
Cys Gln Ile Asp Val Asp Glu Cys Lys Glu Ala Gln His Cys Ser
            140                 145                 150
Gln Lys Cys Val Asn Thr Leu Gly Ser Phe Gln Cys Val Cys Glu
            155                 160                 165
Glu Gly Phe Ser Leu Asp Glu Asp Lys Val Thr Cys Ser Lys Asn
            170                 175                 180
Pro Ala Ser Ser Arg Asn Thr Gly Gly Gly Leu Gly Leu Val Glu
            185                 190                 195
Asn Val Thr Glu Glu Val Gln Ile Leu Lys Asn Arg Val Glu Leu
            200                 205                 210
Leu Glu Gln Lys Leu Glu Met Val Leu Ala Pro Phe Thr Thr Leu
            215                 220                 225
Leu Pro Leu Asp Gly Ala Gly Asp Thr Asn Ser Phe Leu Ser Glu
            230                 235                 240
Arg Thr Asn Phe Leu Ser His Ser Leu Gln Gln Leu Asp Arg Ile
            245                 250                 255
Glu Ser Leu Ser Glu Gln Val Gly Phe Leu Glu Glu Arg Ile Gly
            260                 265                 270
Ala Cys Gly Cys Gln Glu Asn
            275

<210> SEQ ID NO 5
<211> LENGTH: 1364
<212> TYPE: DNA
<213> ORGANISM: Danio rerio

<400> SEQUENCE: 5
cgcgcgacag gtggaccgaa tggcctcggg ctcggcaagg catcacgtga         50
tattattgac agggtagctg attaacagct gtaccagagg caaacagaca        100
cacctgcagt ctctctttct gctgtcagac acacctgaga acagacaga         150
ctgacagaga tgtacacagc acttctgctc tcctcctctc tgtttctcct        200
gcatgtgacc tgcacacctc agactcacag tcatcacggg aggagagtgt        250
gtgttggtga tgtctggagt cgtcgtgtgt cttacagcac agagtctttt        300
cttcagcctg tacacaaacc ctacatcacc atgtgccaaa accaccgcat        350
gtgcagcacg tacaagtaag aacagcacag gaaaacacat atcaaaaccg        400
taccatgcac catcaactca ctgtattgcg tgttttacag gaccatctac        450
aaggtttctt ataggcaggt gaccagagca gctcctaatc tacaaattta        500
cccagaatgc tgtccgggat ggagacgcat gcattcacac aactgcaacc        550
aagcggtatg tgaacagtct tgtgcaaacg gaggctcgtg tgtaaggccc        600
aatcactgtg cctgtctgag aggatggaca ggacgattct gccaaataga        650
tgtggacgag tgtaaggagg ctcagcactg ctctcagaag tgtgtgaata        700
cgctgggcag ttttcaatgt gtgtgtgagg agggattcag tttggacgaa        750
gataaagtca catgttcaaa aaatcctgct tcctcacgga acactggtgg        800
aggtttgggg ttggtggaga cgttactga agaggttcag atcctaaaaa         850
accgagtgga gctcctggag cagaaactgg agatggttct agcacccttc        900
accaccctcc tacctctgga tggagcaggg gacaccaaca gcttcctgtc        950
tgagcgaacc aacttcctgt cccactctct gcagcagctg gaccgcatcg       1000
```

-continued

| | |
|---|---|
| agtcgctcag cgaacaggtc ggcttcctgg aggagagaat cggagcctgt | 1050 |
| ggctgtcagg aaaactagac gatcaacgcc atcactgatc acaggctgac | 1100 |
| ccatcaaaca tgttctcaag aacacgaggg aaatcatgtt gaaactcttt | 1150 |
| atttggcaca cgagccggtg attgatattg ttcatgtcgt gtcatttaac | 1200 |
| tgttgtgtaa gtttgagtca ggagaaatgt aaatttatgt atttataatt | 1250 |
| ccatgttctc gtcatgagtt atgcttttg gataagttgc attccttttt | 1300 |
| tacgtctcat tttgtgtaat aaaactgctt aaatcttaaa aaaaaaaaa | 1350 |
| aaaaaaaaaa aaaa | 1364 |

<210> SEQ ID NO 6
<211> LENGTH: 25
<212> TYPE: DNA
<213> ORGANISM: Artificial sequence
<220> FEATURE:
<223> OTHER INFORMATION: AS-47 antisense oligonucleotide

<400> SEQUENCE: 6
caggtgtgtc tgacagcaga aagag                                25

<210> SEQ ID NO 7
<211> LENGTH: 25
<212> TYPE: DNA
<213> ORGANISM: Artificial sequence
<220> FEATURE:
<223> OTHER INFORMATION: AS195 antisense oligonucleotide

<400> SEQUENCE: 7
tgtgctgttc ttacttgtac gtgct                                25

<210> SEQ ID NO 8
<211> LENGTH: 22
<212> TYPE: DNA
<213> ORGANISM: Artificial sequence
<220> FEATURE:
<223> OTHER INFORMATION: Forward PCR primer

<400> SEQUENCE: 8
tacacagcac ttctgctctc ct                                   22

<210> SEQ ID NO 9
<211> LENGTH: 20
<212> TYPE: DNA
<213> ORGANISM: Artificial sequence
<220> FEATURE:
<223> OTHER INFORMATION: Reverse PCR primer

<400> SEQUENCE: 9
agttgtgtga atgcatgcgt                                      20

<210> SEQ ID NO 10
<211> LENGTH: 25
<212> TYPE: DNA
<213> ORGANISM: Artificial sequence
<220> FEATURE:
<223> OTHER INFORMATION: Control oligonucleotide

<400> SEQUENCE: 10
acgacggtca cgatgaatgg agagt                                25

<210> SEQ ID NO 11

```
<211> LENGTH: 25
<212> TYPE: DNA
<213> ORGANISM: Artificial sequence
<220> FEATURE:
<223> OTHER INFORMATION: Control oligonucleotide

<400> SEQUENCE: 11
cattgttcat cgtcttgttg  cgtgt                                           25
```